(12) United States Patent
Ingram et al.

(10) Patent No.: US 12,408,939 B2
(45) Date of Patent: Sep. 9, 2025

(54) DISRUPTIVE DRESSING FOR USE WITH NEGATIVE PRESSURE AND FLUID INSTILLATION

(71) Applicant: Solventum Intellectual Properties Company, Maplewood, MN (US)

(72) Inventors: Shannon C. Ingram, Bulverde, TX (US); Christopher Brian Locke, Bournemouth (GB); Peter Arnold, Northumberland (GB); Timothy Mark Robinson, Shillingstone (GB); Christopher Allen Carroll, San Antonio, TX (US); Michael E. Manwaring, San Antonio, TX (US)

(73) Assignee: Solventum Intellectual Properties Company, Maplewood, MN (US)

( * ) Notice: Subject to any disclaimer, the term of this patent is extended or adjusted under 35 U.S.C. 154(b) by 1027 days.

(21) Appl. No.: 16/923,651

(22) Filed: Jul. 8, 2020

(65) Prior Publication Data
US 2020/0337719 A1    Oct. 29, 2020

Related U.S. Application Data

(62) Division of application No. 15/884,149, filed on Jan. 30, 2018, now Pat. No. 10,743,900, which is a
(Continued)

(51) Int. Cl.
*A61B 17/32* (2006.01)
*A61B 17/22* (2006.01)
(Continued)

(52) U.S. Cl.
CPC ........ *A61B 17/32* (2013.01); *A61B 17/22004* (2013.01); *A61F 13/05* (2024.01);
(Continued)

(58) Field of Classification Search
CPC ........ A61B 17/32; A61B 2017/320008; A61B 2017/32006; A61B 2017/320064;
(Continued)

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

(Continued)

*Primary Examiner* — Brigid K Byrd

(57) ABSTRACT

A method and apparatus for disrupting material at a tissue site is described. A contact layer may be selected for use on the tissue site and positioned adjacent to the tissue site. The contact layer may include walls defining a plurality of through-holes. A sealing member may be positioned over the contact layer and sealed to tissue surrounding the tissue site to form a sealed space enclosing the contact layer. A negative-pressure source may be fluidly coupled to the sealed space. The negative-pressure source may supply negative pressure to the sealed space and the contact layer to draw tissue into the through-holes to form nodules. The negative pressure may be vented from the sealed space to release the nodules.

17 Claims, 13 Drawing Sheets
(3 of 13 Drawing Sheet(s) Filed in Color)

Related U.S. Application Data division of application No. 14/708,109, filed on May 8, 2015, now Pat. No. 9,918,733.

(60) Provisional application No. 61/991,150, filed on May 9, 2014, provisional application No. 61/991,174, filed on May 9, 2014, provisional application No. 61/991,134, filed on May 9, 2014.

(51) Int. Cl.
  *A61F 13/05* (2024.01)
  *A61M 1/00* (2006.01)
  *A61M 27/00* (2006.01)

(52) U.S. Cl.
  CPC .............. *A61M 1/915* (2021.05); *A61M 1/92* (2021.05); *A61M 27/00* (2013.01); *A61B 2017/22008* (2013.01); *A61B 2017/22089* (2013.01); *A61B 2017/320008* (2013.01); *A61B 2017/32006* (2013.01); *A61B 2017/320064* (2013.01); *A61M 1/96* (2021.05)

(58) Field of Classification Search
  CPC .... A61B 17/22004; A61B 2017/22008; A61B 2017/22089; A61F 13/00068; A61F 13/00042; A61F 13/00029; A61F 13/0216; A61F 2013/00255; A61F 13/05; A61M 27/00; A61M 1/90; A61M 1/92; A61M 1/015; A61M 1/96
  See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,683,921 A | 8/1972 | Brooks et al. |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,902,565 A | 2/1990 | Brook |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,765,123 B2 | 7/2004 | de Jong et al. |
| 6,814,079 B2 | 11/2004 | Heaton et al. |
| 7,381,859 B2 | 6/2008 | Hunt et al. |
| 7,846,141 B2 | 12/2010 | Weston |
| 7,951,124 B2 | 5/2011 | Boehringer et al. |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,168,180 B2 | 10/2015 | Ha et al. |
| 9,198,801 B2 | 12/2015 | Weston |

(56) References Cited

U.S. PATENT DOCUMENTS

| | | |
|---|---|---|
| 9,211,365 B2 | 12/2015 | Weston |
| 9,289,542 B2 | 3/2016 | Blott et al. |
| 9,421,309 B2 | 8/2016 | Robinson et al. |
| 9,918,733 B2 | 3/2018 | Ingram et al. |
| 9,974,694 B2 | 5/2018 | Locke et al. |
| 10,369,058 B2 | 8/2019 | Ha et al. |
| 10,610,414 B2 | 4/2020 | Hartwell et al. |
| 10,736,788 B2 | 8/2020 | Locke et al. |
| 10,743,900 B2 | 8/2020 | Ingram et al. |
| 11,224,542 B2 | 1/2022 | Robinson et al. |
| 2001/0037118 A1 | 11/2001 | Shadduck |
| 2002/0065494 A1 | 5/2002 | Lockwood et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2002/0161346 A1 | 10/2002 | Lockwood et al. |
| 2004/0030304 A1 | 2/2004 | Hunt et al. |
| 2005/0282895 A1 | 12/2005 | Dosch et al. |
| 2007/0185426 A1 | 8/2007 | Ambrosio et al. |
| 2008/0132819 A1 | 6/2008 | Radl et al. |
| 2008/0177253 A1* | 7/2008 | Boehringer ....... A61F 13/00021 602/47 |
| 2008/0275409 A1 | 11/2008 | Kane et al. |
| 2008/0300555 A1 | 12/2008 | Olson et al. |
| 2009/0012482 A1 | 1/2009 | Pinto et al. |
| 2009/0093779 A1* | 4/2009 | Riesinger ............ A61F 13/0243 604/290 |
| 2009/0227969 A1 | 9/2009 | Jaeb et al. |
| 2009/0299303 A1 | 12/2009 | Seegert |
| 2010/0063484 A1 | 3/2010 | Heagle |
| 2010/0160871 A1* | 6/2010 | Seegert .......... C12Y 304/22003 604/290 |
| 2010/0160874 A1 | 6/2010 | Robinson et al. |
| 2010/0160876 A1 | 6/2010 | Robinson et al. |
| 2010/0185163 A1 | 7/2010 | Heagle |
| 2010/0312159 A1 | 12/2010 | Aali et al. |
| 2011/0054422 A1 | 3/2011 | Locke et al. |
| 2011/0087176 A2 | 4/2011 | Blott et al. |
| 2011/0118683 A1 | 5/2011 | Weston |
| 2011/0178451 A1 | 7/2011 | Robinson et al. |
| 2011/0213287 A1 | 9/2011 | Lattimore et al. |
| 2011/0213319 A1 | 9/2011 | Blott et al. |
| 2011/0230809 A1 | 9/2011 | Manwaring et al. |
| 2011/0282309 A1 | 11/2011 | Adie et al. |
| 2011/0301556 A1 | 12/2011 | Lichtenstein |
| 2012/0016334 A1 | 1/2012 | Nakajima et al. |
| 2012/0143113 A1* | 6/2012 | Robinson ............... A61M 1/964 604/319 |
| 2012/0143114 A1 | 6/2012 | Locke et al. |
| 2012/0157945 A1 | 6/2012 | Robinson et al. |
| 2013/0144230 A1 | 6/2013 | Wu et al. |
| 2013/0165821 A1* | 6/2013 | Freedman ................ A61M 1/77 604/20 |
| 2013/0211349 A1 | 8/2013 | Stokes et al. |
| 2013/0274717 A1 | 10/2013 | Dunn |
| 2014/0066868 A1 | 3/2014 | Freedman et al. |
| 2014/0155791 A1 | 6/2014 | Robinson et al. |
| 2014/0163491 A1 | 6/2014 | Schuessler et al. |
| 2014/0228787 A1 | 8/2014 | Croizat et al. |
| 2014/0236112 A1 | 8/2014 | Von Wolff et al. |
| 2015/0080788 A1 | 3/2015 | Blott et al. |
| 2015/0119832 A1 | 4/2015 | Locke |
| 2015/0174284 A1 | 6/2015 | Payne et al. |
| 2015/0190288 A1* | 7/2015 | Dunn ................ A61F 13/00068 604/319 |
| 2015/0201954 A1 | 7/2015 | Pratt et al. |
| 2015/0320434 A1 | 11/2015 | Ingram et al. |
| 2015/0320602 A1 | 11/2015 | Locke et al. |
| 2015/0320603 A1 | 11/2015 | Locke et al. |
| 2016/0022885 A1 | 1/2016 | Dunn et al. |
| 2016/0038345 A1 | 2/2016 | Ha et al. |
| 2016/0095754 A1 | 4/2016 | Andrews et al. |
| 2016/0158066 A1 | 6/2016 | Chao |
| 2016/0354086 A1* | 12/2016 | Dunn ..................... A61M 1/915 |
| 2017/0007462 A1* | 1/2017 | Hartwell ........... A61F 13/00034 |
| 2017/0135862 A1 | 5/2017 | Tuck et al. |
| 2017/0189237 A1 | 7/2017 | Locke et al. |
| 2017/0197006 A1 | 7/2017 | Johnson et al. |
| 2017/0231822 A1 | 8/2017 | Hoggarth et al. |
| 2017/0239095 A1 | 8/2017 | Hoggarth et al. |
| 2018/0235646 A1 | 8/2018 | Locke et al. |
| 2018/0353337 A1 | 12/2018 | Locke |
| 2018/0353338 A1 | 12/2018 | Locke et al. |
| 2018/0353662 A1 | 12/2018 | Locke et al. |
| 2019/0117465 A1 | 4/2019 | Osborne et al. |
| 2019/0192350 A1 | 6/2019 | Gowans et al. |
| 2019/0231944 A1 | 8/2019 | Dunn et al. |
| 2019/0274889 A1 | 9/2019 | Steward et al. |
| 2019/0314209 A1 | 10/2019 | Ha et al. |
| 2020/0046567 A1 | 2/2020 | Carroll et al. |
| 2020/0107965 A1 | 4/2020 | Greener |
| 2020/0146896 A1 | 5/2020 | Rice et al. |
| 2020/0155359 A1 | 5/2020 | Carroll et al. |
| 2020/0383837 A1 | 12/2020 | Gowans et al. |
| 2021/0077302 A1 | 3/2021 | Carroll et al. |
| 2021/0228417 A1 | 7/2021 | Ha et al. |
| 2023/0000687 A1 | 1/2023 | Rice et al. |
| 2023/0000688 A1 | 1/2023 | Rice et al. |
| 2024/0099898 A1 | 3/2024 | Rice et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| DE | 102006017194 A1 | 10/2007 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| EP | 2098257 A1 | 9/2009 |
| EP | 3263079 A1 | 1/2018 |
| EP | 3378450 A1 | 9/2018 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| GB | 2365350 A | 2/2002 |
| GB | 2377939 A | 1/2003 |
| JP | S57-013040 A | 1/1982 |
| JP | 4129536 B2 | 8/2008 |
| NO | 90/010424 A1 | 9/1990 |
| SG | 71559 | 4/2002 |
| WO | 80/02182 A1 | 10/1980 |
| WO | 87/04626 A1 | 8/1987 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 0185248 A1 | 11/2001 |
| WO | 2005102234 A2 | 11/2005 |
| WO | 2006114638 A2 | 11/2006 |
| WO | 2008005532 A2 | 1/2008 |
| WO | 2008136998 A1 | 11/2008 |
| WO | 2009021523 A1 | 2/2009 |
| WO | 2009/146441 A1 | 12/2009 |
| WO | 2010051071 A1 | 5/2010 |
| WO | 2010051073 A1 | 5/2010 |
| WO | 2010075178 A2 | 7/2010 |
| WO | 2011008497 A2 | 1/2011 |
| WO | 2011089098 A1 | 7/2011 |
| WO | 2013032745 A1 | 3/2013 |
| WO | 2013066426 A2 | 5/2013 |
| WO | 2013071243 A2 | 5/2013 |
| WO | 2013116552 A1 | 8/2013 |

(56) References Cited

FOREIGN PATENT DOCUMENTS

| | | |
|---|---|---|
| WO | 2013129343 A1 | 9/2013 |
| WO | 2013149078 A1 | 10/2013 |
| WO | 2014/014922 A1 | 1/2014 |
| WO | 2014014871 A1 | 1/2014 |
| WO | 2014024048 A1 | 2/2014 |
| WO | 2014143487 A1 | 9/2014 |
| WO | 2015172104 A1 | 11/2015 |
| WO | 2015172111 A1 | 11/2015 |
| WO | 2015173547 A1 | 11/2015 |
| WO | 2017195038 A1 | 11/2017 |
| WO | 2018/077872 A1 | 5/2018 |
| WO | 2018/094061 A1 | 5/2018 |
| WO | 2018/226328 A1 | 12/2018 |
| WO | 2019136164 A1 | 7/2019 |
| WO | 2019152422 A1 | 8/2019 |
| WO | 2020097529 A1 | 5/2020 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, The Use of Hypermia in the Postoperative Treatment of Lesions of the Extremities and Thorax, Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians; Jul. 2007.

International Search Report and Written Opinion for PCT/US2015/030027 mailed Jul. 15, 2015.

(56) References Cited

OTHER PUBLICATIONS

Partial International Search Report from PCT/US2015/030030 mailed Jul. 22, 2015.
International Search Report and Written Opinion for PCT/US2015/030023 mailed Aug. 24, 2015.
Extended European Search Report for corresponding Application No. 171862527, mailed Nov. 14, 2017.
"Introduction to Polyurethanes: Thermoplastic Polyurethane", American Chemistry Council, https://polyurethane.americanchemistry.com/polyurethanes/Introduction-to-Polyurethanes/Applications/Thermoplastic-Polyurethane/.
International Search Report and Written Opinion for corresponding Application No. PCT/US2019/027463, mailed Jul. 4, 2019.
Japanese Notice of Rejection for corresponding Application No. 2016-566815, mailed Feb. 5, 2019.
Extended European Search Report for corresponding Application No. 18162504.7, mailed May 24, 2018.
Japanese Notice of Rejection for corresponding Application No. 2016-566785, mailed Jun. 25, 2019.
Japanese Notice of Rejection for corresponding Application No. 2016-566785, mailed Jan. 29, 2019.
Non-Final Office Action for Corresponding U.S. Appl. No. 15/960,310, mailed Apr. 29, 2020.
Japanese Notice of Rejection for Corresponding Application No. 2019-233695, mailed Oct. 13, 2020.
International Search Report and Written Opinion for Corresponding Application No. PCT/US2019/060567, mailed Feb. 14, 2020.
International Search Report and Written Opinion for Corresponding Application No. PCT/US2019/045505, mailed Nov. 7, 2019.
International Search Report and Written Opinion for Corresponding Application No. PCT/US2019/060479, mailed Apr. 7, 2020.
International Search Report and Written Opinion for Corresponding Application No. PCT/US2020/013922, mailed May 4, 2020.
Chinese Notice of Rejection Corresponding to Application No. 2020800099951, mailed Mar. 28, 2022.
International Search Report and Written Opinion for Corresponding Application No. PCT/IB2020/056911, mailed Oct. 21, 2020.
International Search Report and Written Opinion Corresponding to Application No. PCT/IB2020/061435, mailed Mar. 16, 2021.
International Search Report and Written Opinion Corresponding to Application No. PCT/IB2020/061465, mailed Mar. 16, 2021.
International Search Report and Written Opinion Corresponding to Application No. PCT/IB2020/061540, mailed Feb. 24, 2021.
Canadian Examination Report for related application 2,947,302, dated Jun. 11, 2021.
Japanese Notice of Rejection for related application 2020-557257, dated Feb. 28, 2023.
Office Action for related U.S. Appl. No. 16/678,450, dated Jul. 31, 2023.
Office action for related U.S. Appl. No. 16/918,682, dated Sep. 21, 2023.
Japanese Notice of Rejection for Application No. 2021-542412, dated Dec. 5, 2023.
European Examination Report for Application No. 20747133.5, dated Dec. 21, 2023.
Japanese Notice of Rejection for Application No. 2019-233695 dated Mar. 5, 2024.
Office action for related U.S. Appl. No. 17/629,174, dated Mar. 26, 2024.
Office action for U.S. Appl. No. 16/678,450, dated Sep. 9, 2024.
Japanese Notice of Rejection for Application No. 2021-524440 dated Apr. 16, 2024.
Office action for U.S. Appl. No. 16/745,075, dated Jul. 24, 2024.
Japanese Decision of Rejection and Decision for Dismissal of Amendment for Application No. 2021-524440, dated Oct. 15, 2024.
Office action for U.S. Appl. No. 16/918,682, dated Jan. 2, 2025.
Copper Development Association Inc., Introduction to Antimicrobial Copper, Feb. 15, 2024.
Office action for U.S. Appl. No. 17/629,174, dated Feb. 26, 2025.
Office action for U.S. Appl. No. 17/779,755, dated Apr. 9, 2025.
Office action for U.S. Appl. No. 17/779,792, dated Jun. 3, 2025.

* cited by examiner

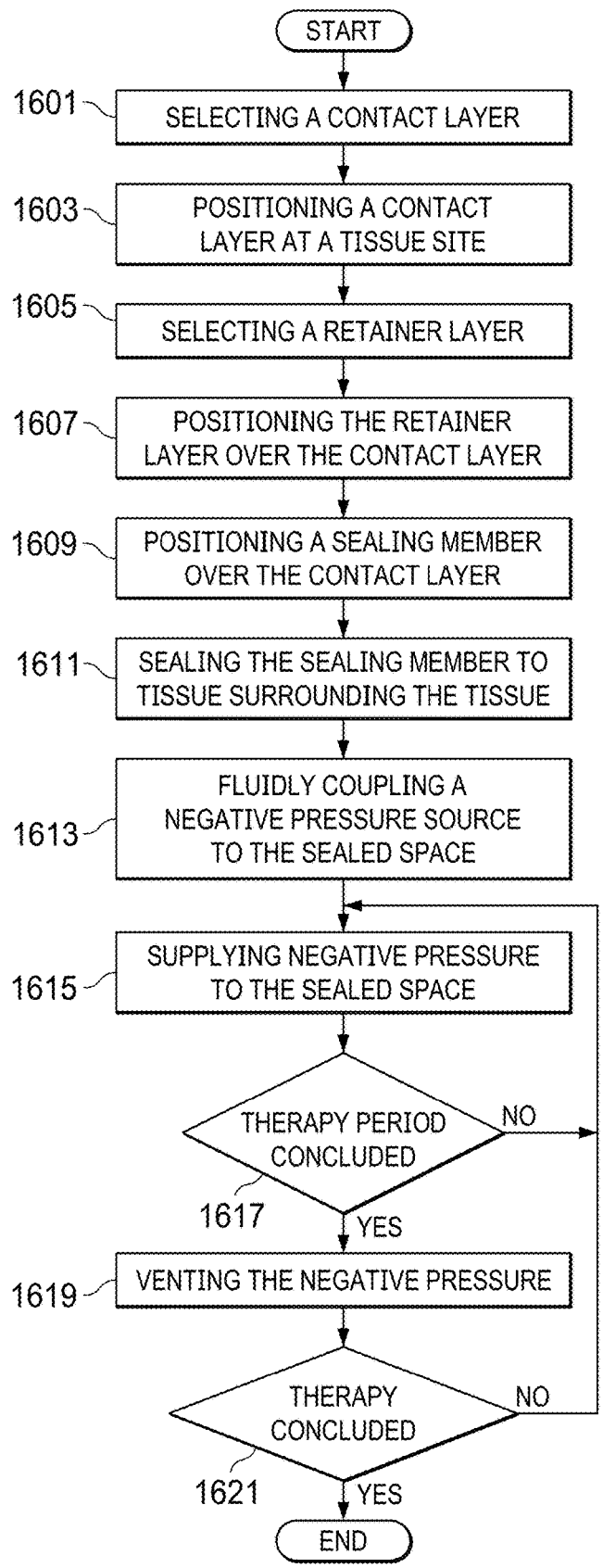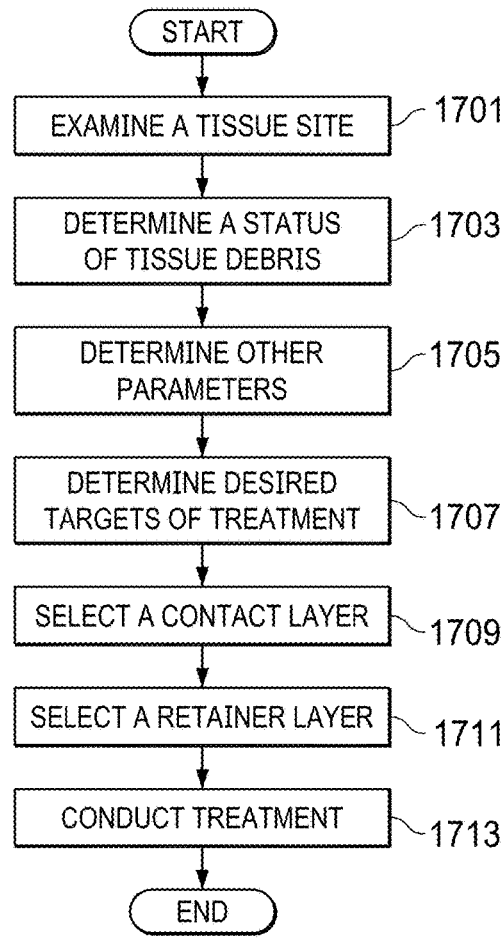
FIG. 16
FIG. 17

DISRUPTIVE DRESSING FOR USE WITH NEGATIVE PRESSURE AND FLUID INSTILLATION

RELATED APPLICATIONS

This application is a divisional of U.S. patent application Ser. No. 15/884,149, filed Jan. 30, 2018, which is a divisional of U.S. patent application Ser. No. 14/708,109, filed May 8, 2015, now U.S. Pat. No. 9,918,733, which claims the benefit, under 35 USC § 119(e), of the filing of U.S. Provisional Patent Application Ser. No. 61/991,150, entitled "Subcutaneous Anchor for Surgical Closure," by Locke et al., filed May 9, 2014; U.S. Provisional Patent Application Ser. No. 61/991,174, entitled "Dressing with Contracting Layer for Linear Tissue Sites," by Locke et al., filed May 9, 2014; and U.S. Provisional Patent Application Ser. No. 61/991,134, entitled "Debriding Dressing for use with Negative Pressure and Fluid Instillation," by Locke et al., filed May 9, 2014, all of which are incorporated herein by reference for all purposes.

TECHNICAL FIELD

The invention set forth in the appended claims relates generally to tissue treatment systems and more particularly, but without limitation, to a dressing for disrupting non-viable tissue at a tissue site.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," and "vacuum-assisted closure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, the cost and complexity of negative-pressure therapy can be a limiting factor in its application, and the development and operation of negative-pressure systems, components, and processes continue to present significant challenges to manufacturers, healthcare providers, and patients.

Often debris located in or on a tissue site may hinder the application of beneficial therapy, increasing healing times and the risk of further tissue damage. Debris can include necrotic tissue, foreign bodies, biofilms, slough, eschar, and other debris that can negatively impact tissue healing. Removal of the tissue debris can be accomplished through debridement processes; however, debridement processes can be painful to a patient and may result in further damage to the tissue site. Debriding a tissue site can also be a time-consuming process that may significantly delay the application of other beneficial therapies, such as negative-pressure therapy or instillation therapy. The development of systems, components, and processes to aid in the removal of debris to decrease healing times and increase positive patient outcomes continue to present significant challenges to manufacturers, healthcare providers, and patients.

SUMMARY

New and useful systems, apparatuses, and methods for disrupting non-viable tissue at a tissue site in a negative-pressure therapy and instillation environment are set forth in the appended claims. Illustrative embodiments are also provided to enable a person skilled in the art to make and use the claimed subject matter. For example, a method for disrupting material at a tissue site is described. A contact layer may be selected for use on the tissue site and positioned adjacent to the tissue site. The contact layer may include walls defining a plurality of through-holes. A sealing member may be positioned over the contact layer and sealed to tissue surrounding the tissue site to form a sealed space enclosing the contact layer. A negative-pressure source may be fluidly coupled to the sealed space. The negative-pressure source may supply negative pressure to the sealed space and the contact layer to draw tissue into the through-holes to form nodules. The negative pressure may be vented from the sealed space to release the nodules.

Alternatively, another example embodiment includes a system for softening materials at a tissue site. The system may include a contact layer formed from a compressible material and configured to be positioned adjacent the tissue site. The contact layer may include a plurality of through-holes. The system may also include a cover adapted to form a sealed space over the contact layer and the tissue site for receiving a negative pressure from a negative-pressure source. The through-holes may be configured to receive tissue in the through-holes in response to negative pressure in the sealed space to form nodules in the tissue site.

Other embodiments also include an apparatus for disrupting debris in a tissue site. The apparatus may include a contact layer formed from a felted foam and having a plurality of through-holes separated from each other by walls. The through-holes may be configured to form nodules in the tissue site in response to negative pressure.

A method for selecting a tissue interface for tissue disruption is also described. A status of debris in the tissue site can be determined along with other parameters influencing treatment of the tissue site. In response to determining a status of debris and other parameters influencing treatment, desired targets of treatment can be determined. In response to the desired targets of treatment, a contact layer can be selected.

A system for debriding a tissue site is also described. The system can include a manifold adapted to deliver negative pressure to the tissue site. The system can also include a cover adapted to form a sealed space over the manifold and the tissue site for receiving a negative pressure from a negative-pressure source. The system can further include a debridement tool adapted to be positioned between the manifold and the tissue site. The debridement tool can have a tissue-facing surface and an opposite surface including a plurality of holes extending therebetween. The holes can be separated from each other by walls, and the walls can have transverse surfaces extending between the tissue-facing surface and the opposite surface that form cutting edges with the tissue-facing surface. The holes can have a perforation shape factor that allows the holes to collapse from a relaxed position to a contracted position in response to an application and removal of negative pressure from the sealed space. The cutting edges can be adapted to debride the tissue site in response to movement of the debridement tool between the relaxed position and the contracted position.

Objectives, advantages, and a preferred mode of making and using the claimed subject matter may be understood best by reference to the accompanying drawings in conjunction with the following detailed description of illustrative embodiments.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A is a detail view of a portion of the therapy system of FIG. 1;

FIG. 16 is a flow chart 1600 illustrating exemplary operations that can be associated with some embodiments of the therapy system 100 of FIG. 1; and FIG. 17 is a flow chart 1700 illustrating exemplary operations that can be associated with some embodiments of the therapy system 100 of FIG. 1.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
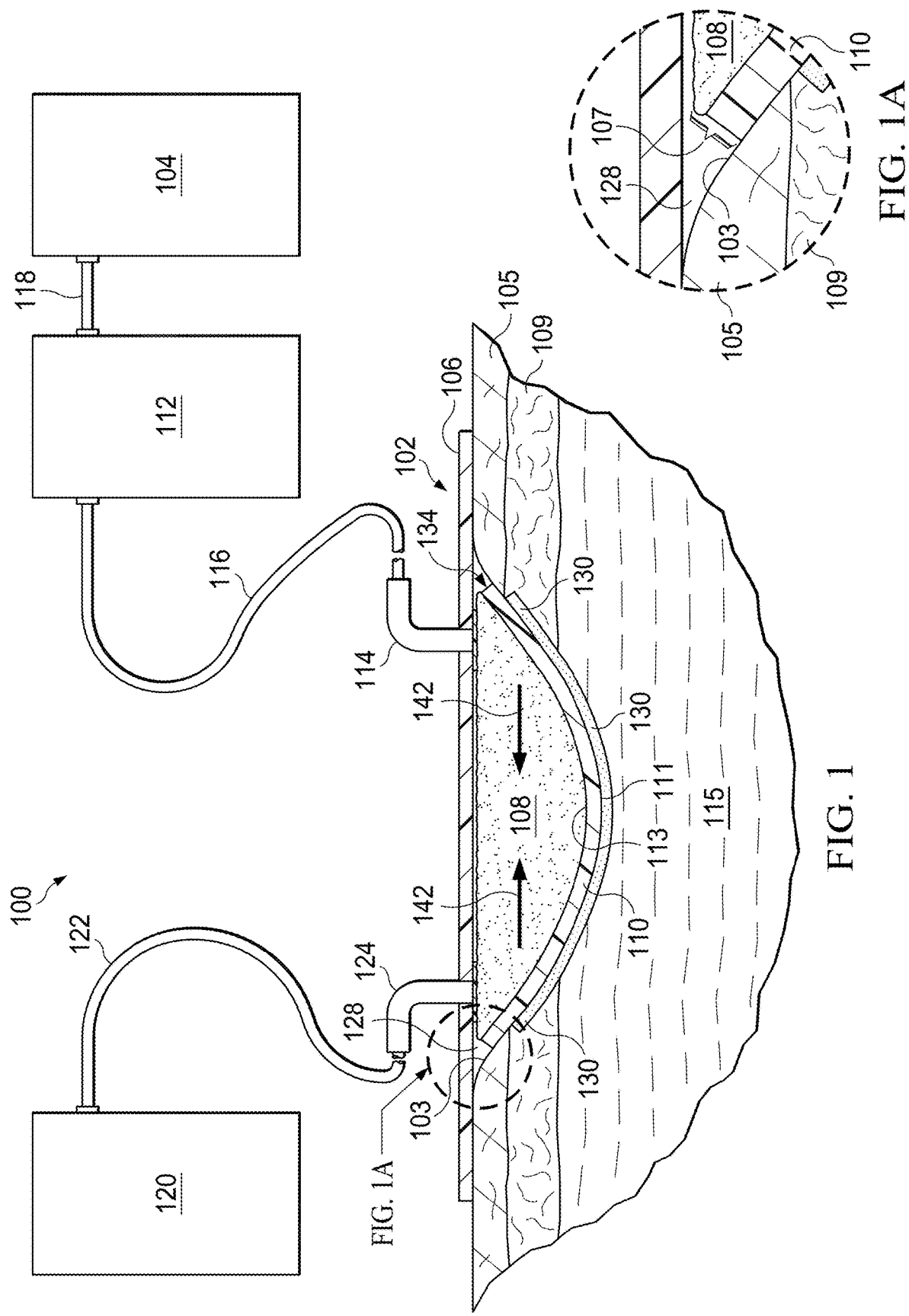
FIG. 1 is a sectional section view with a portion shown in elevation, illustrating details that may be associated with some embodiments of a therapy system.

FIG. 1 is a sectional view, with a portion shown in elevation, of an example embodiment of a therapy system 100 that can provide negative pressure therapy, instillation of topical treatment solutions, and disruption of debris on tissue in accordance with this specification. The therapy system 100 may include a dressing and a negative-pressure source. For example, a dressing 102 may be fluidly coupled to a negative-pressure source 104, as illustrated in FIG. 1. FIG. 1A is a detail view of a portion of the therapy system 100 of FIG. 1. As shown in FIG. 1 and FIG. 1A, the dressing 102, for example, includes a cover, such as a drape 106, and a tissue interface 107 for positioning adjacent to or proximate to a tissue site such as, for example, a tissue site 103. In some embodiments, the tissue interface 107 may be a cover layer, such as a retainer layer 108. The tissue interface 107 can also be a contact layer 110 having a tissue-facing surface 111 adapted to face the tissue site 103 and an opposite surface 113 adapted to face, for example, the retainer layer 108. In some embodiments, the tissue interface 107 can be both the retainer layer 108 and the contact layer 110, and the retainer layer 108 and the contact layer 110 may be integral components. In other embodiments, the tissue interface 107 can include the retainer layer 108 and the contact layer 110, and the retainer layer and the contact layer 110 may be separate components as shown in FIG. 1. The therapy system 100 may also include an exudate container, such as a container 112, coupled to the dressing 102 and to the negative-pressure source 104. In some embodiments, the container 112 may be fluidly coupled to the dressing 102 by a connector 114 and a tube 116, and the container 112 may be fluidly coupled to the negative-pressure source 104 by a tube 118.

In some embodiments, the therapy system 100 may also include an instillation solution source. For example, a fluid source 120 may be fluidly coupled to the dressing 102 by a tube 122 and a connector 124, as illustrated in the example embodiment of FIG. 1.

In general, components of the therapy system 100 may be coupled directly or indirectly. For example, the negative-pressure source 104 may be directly coupled to the container 112 and indirectly coupled to the dressing 102 through the container 112. Components may be fluidly coupled to each other to provide a path for transferring fluids (i.e., liquid and/or gas) between the components.

In some embodiments, components may be fluidly coupled through a tube, such as the tube 116, the tube 118, and the tube 122. A "tube," as used herein, broadly refers to a tube, pipe, hose, conduit, or other structure with one or more lumina adapted to convey a fluid between two ends. Typically, a tube is an elongated, cylindrical structure with some flexibility, but the geometry and rigidity may vary. Components may also be fluidly coupled without the use of a tube, for example, by having surfaces in contact with or proximate to each other. In some embodiments, components may additionally or alternatively be coupled by virtue of physical proximity, being integral to a single structure, or being formed from the same piece of material. In some embodiments, components may be coupled by being positioned adjacent to each other or by being operable with each other. Coupling may also include mechanical, thermal, electrical, or chemical coupling (such as a chemical bond) in some contexts.

In operation, the tissue interface 107 may be placed within, over, on, or otherwise proximate to the tissue site 103. The drape 106 may be placed over the tissue interface 107 and sealed to tissue near the tissue site. For example, the drape 106 may be sealed to undamaged epidermis peripheral to a tissue site, also known as peritissue. Thus, the dressing 102 can provide a sealed therapeutic environment 128 proximate to a tissue site, substantially isolated from the external environment, and the negative-pressure source 104 can reduce the pressure in the sealed therapeutic environment 128. Negative pressure applied across the tissue site 103 through the tissue interface 107 in the sealed therapeutic environment 128 can induce macrostrain and microstrain in the tissue site 103, as well as remove exudates and other fluids from the tissue site 103, which can be collected in container 112 and disposed of properly.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art.

In general, fluids flow toward lower pressure along a fluid path. Thus, the term "downstream" typically refers to a position in a fluid path that is closer to a source of negative pressure or alternatively further away from a source of positive pressure. Conversely, the term "upstream" refers to a position in a fluid path further away from a source of negative pressure or closer to a source of positive pressure. Similarly, it may be convenient to describe certain features in terms of fluid "inlet" or "outlet" in such a frame of reference, and the process of reducing pressure may be described illustratively herein as "delivering," "distributing," or "generating" reduced pressure, for example. This orientation is generally presumed for purposes of describing various features and components of systems herein.

The term "tissue site," such as the tissue site 103, in this context broadly refers to a wound or defect located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of tissue that are not necessarily wounded or defective, but are instead areas in which it may be desirable to add or promote the growth of additional tissue. For example, negative pressure may be used in certain tissue areas to grow additional tissue that may be harvested and transplanted to another tissue location. As shown in FIG. 1, the tissue site 103 may extend through an epidermis 105, a dermis 109, and into subcutaneous tissue 115.

"Negative pressure" generally refers to a pressure less than a local ambient pressure, such as the ambient pressure in a local environment external to the sealed therapeutic environment 128 provided by the dressing 102. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure.

A negative-pressure source, such as the negative-pressure source 104, may be a reservoir of air at a negative pressure, or may be a manual or electrically-powered device that can reduce the pressure in a sealed volume, such as a vacuum pump, a suction pump, a wall suction port available at many healthcare facilities, or a micro-pump, for example. A negative-pressure source can also include a tablet, solution, spray, or other delivery mechanism that can initiate a chemical reaction to generate negative pressure. A negative-pressure source can also include a pressurized gas cylinder, such as a $CO_2$ cylinder used to drive a pump to produce negative pressure. A negative-pressure source may be housed within or used in conjunction with other components, such as sensors, processing units, alarm indicators, memory, databases, software, display devices, or user interfaces that further facilitate negative-pressure therapy. While the amount and nature of negative pressure applied to a tissue site may vary according to therapeutic requirements, the pressure is generally a low vacuum, also commonly referred to as a rough vacuum, between −5 mmHg (−667 Pa) and −500 mmHg (−66.7 kPa). Common therapeutic ranges are between −25 mmHg (−3.3 kPa) and about −350 mmHg (−46.6 kPa) and more commonly between −75 mmHg (−9.9 kPa) and −300 mmHg (−39.9 kPa).

A "connector," such as the connector 114 and the connector 124, may be used to fluidly couple a tube to the sealed therapeutic environment 128. The negative pressure developed by a negative-pressure source may be delivered through a tube to a connector. In one illustrative embodiment, a connector may be a T.R.A.C.® Pad or Sensa T.R.A.C.® Pad available from KCI of San Antonio, Texas. In one exemplary embodiment, the connector 114 may allow the negative pressure generated by the negative-pressure source 104 to be delivered to the sealed therapeutic environment 128. In other exemplary embodiments, a connector may also be a tube inserted through a drape. In one exemplary embodiment, the connector 124 may allow fluid provided by the fluid source 120 to be delivered to the sealed therapeutic environment 128. In one illustrative embodiment, the connector 114 and the connector 124 may be combined in a single device, such as a Vera T.R.A.C.® Pad available from KCI of San Antonio, Texas. In some embodiments, the connector 114 and the connector 124 may include one or more filters to trap particles entering and leaving the sealed therapeutic environment 128.

The tissue interface 107 can be generally adapted to contact a tissue site. The tissue interface 107 may be partially or fully in contact with the tissue site. If the tissue site is a wound, for example, the tissue interface 107 may partially or completely fill the wound, or may be placed over the wound. The tissue interface 107 may take many forms, and may have many sizes, shapes, or thicknesses depending on a variety of factors, such as the type of treatment being implemented or the nature and size of a tissue site. For example, the size and shape of the tissue interface 107 may be adapted to the contours of deep and irregular shaped tissue sites. In some embodiments, the tissue interface 107 may be provided in a spiral cut sheet. Moreover, any or all of the surfaces of the tissue interface 107 may have an uneven, coarse, or jagged profile that can induce microstrains and stresses at a tissue site.

In some embodiments, the tissue interface 107 may include the retainer layer 108, the contact layer 110, or both and may also be a manifold. A "manifold" in this context generally includes any substance or structure providing a plurality of pathways adapted to collect or distribute fluid across a tissue site under negative pressure. For example, a manifold may be adapted to receive negative pressure from a source and distribute the negative pressure through multiple apertures across a tissue site, which may have the effect of collecting fluid from across a tissue site and drawing the fluid toward the source. In some embodiments, the fluid path may be reversed or a secondary fluid path may be provided to facilitate delivering fluid across a tissue site.

In some illustrative embodiments, the pathways of a manifold may be channels interconnected to improve distribution or collection of fluids across a tissue site. For example, cellular foam, open-cell foam, reticulated foam, porous tissue collections, and other porous material such as gauze or felted material generally include pores, edges, and/or walls adapted to form interconnected fluid pathways. Liquids, gels, and other foams may also include or be cured to include apertures and flow channels. In some illustrative embodiments, a manifold may be a porous foam material having interconnected cells or pores adapted to uniformly (or quasi-uniformly) distribute negative pressure to a tissue site. The foam material may be either hydrophobic or hydrophilic. The pore size of a foam material may vary according to needs of a prescribed therapy. For example, in some embodiments, the retainer layer 108 may be a foam having pore sizes in a range of about 60 microns to about 2000 microns. In other embodiments, the retainer layer 108 may be a foam having pore sizes in a range of about 400 microns to about 600 microns. The tensile strength of the retainer layer 108 may also vary according to needs of a prescribed therapy. For example, the tensile strength of a foam may be increased for instillation of topical treatment solutions. In one non-limiting example, the retainer layer 108 may be an open-cell, reticulated polyurethane foam such as GranuFoam® dressing available from Kinetic Concepts, Inc. of San Antonio, Texas; in other embodiments the retainer layer 108 may be an open-cell, reticulated polyurethane foam such as a V.A.C. VeraFlo® foam, also available from Kinetic Concepts, Inc., of San Antonio, Texas. In other embodiments, the retainer layer 108 may be formed of an un-reticulated open-cell foam.

In an example in which the tissue interface 107 may be made from a hydrophilic material, the tissue interface 107 may also wick fluid away from a tissue site, while continuing to distribute negative pressure to the tissue site. The wicking properties of the tissue interface 107 may draw fluid away from a tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Texas Other hydrophilic foams may include those made from polyether. Other foams that may exhibit hydrophilic characteristics include hydrophobic foams that have been treated or coated to provide hydrophilicity.

In some embodiments, the tissue interface 107 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The tissue interface 107 may further serve as a scaffold for new cell-growth, or a scaffold material may be used in conjunction with the tissue interface 107 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the drape 106 may provide a bacterial barrier and protection from physical trauma. The drape 106 may also be sealing member constructed from a material that can reduce evaporative losses and provide a fluid seal between two components or two environments, such as between a therapeutic environment and a local external environment. The drape 106 may be, for example, an elastomeric film or membrane that can provide a seal adequate to maintain a negative pressure at a tissue site for a given negative-pressure source. In some example embodiments, the drape 106 may be a polymer drape, such as a polyurethane film, that is permeable to water vapor but impermeable to liquid. Such drapes typically have a thickness in the range of about 25 microns to about 50 microns. For permeable materials, the permeability generally should be low enough that a desired negative pressure may be maintained.

An attachment device may be used to attach the drape 106 to an attachment surface, such as undamaged epidermis, a gasket, or another cover. The attachment device may take many forms. For example, an attachment device may be a medically-acceptable, pressure-sensitive adhesive that extends about a periphery, a portion, or an entire sealing member. In some embodiments, for example, some or all of the drape 106 may be coated with an acrylic adhesive having a coating weight between about 25 grams per square meter (gsm) to about 65 gsm. Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The container 112 is representative of a container, canister, pouch, or other storage component that can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

The fluid source 120 may be representative of a container, canister, pouch, bag, or other storage component that can provide a solution for instillation therapy. Compositions of solutions may vary according to prescribed therapy, but examples of solutions that are suitable for some prescriptions include hypochlorite-based solutions, silver nitrate (0.5%), sulfur-based solutions, biguanides, cationic solutions, and isotonic solutions. In some embodiments, a fluid source, such as the fluid source 120, may be a reservoir of fluid at an atmospheric or greater pressure, or may be a manual or electrically-powered device, such as a pump, that can convey fluid to a sealed volume, such as the sealed therapeutic environment 128, for example. In some embodiments, a fluid source may include a peristaltic pump.

During treatment of a tissue site, a biofilm may develop on or in the tissue site. Biofilms can comprise a microbial infection that can cover a tissue site and impair healing of the tissue site, such as the tissue site 103. Biofilms can also lower the effectiveness of topical antibacterial treatments by preventing the topical treatments from reaching the tissue site. The presence of biofilms can increase healing times, reduce the efficacy and efficiency of various treatments, and increase the risk of a more serious infection.

Even in the absence of biofilms, some tissue sites may not heal according to the normal medical protocol and may develop areas of necrotic tissue. Necrotic tissue may be dead tissue resulting from infection, toxins, or trauma that caused the tissue to die faster than the tissue can be removed by the normal body processes that regulate the removal of dead tissue. Sometimes, necrotic tissue may be in the form of slough, which may include a viscous liquid mass of tissue. Generally, slough is produced by bacterial and fungal infections that stimulate an inflammatory response in the tissue. Slough may be a creamy yellow color and may also be referred to as pus. Necrotic tissue may also include eschar. Eschar may be a portion of necrotic tissue that has become dehydrated and hardened. Eschar may be the result of a burn injury, gangrene, ulcers, fungal infections, spider bites, or anthrax. Eschar may be difficult to move without the use of surgical cutting instruments.

The tissue site 103 may include biofilms, necrotic tissue, lacerated tissue, devitalized tissue, contaminated tissue, damaged tissue, infected tissue, exudate, highly viscous exudate, fibrinous slough and/or other material that can generally be referred to as debris 130. The debris 130 may inhibit the efficacy of tissue treatment and slow the healing of the tissue site 103. As shown in FIG. 1, the debris 130 may cover all or a portion of the tissue site 103. If the debris is in the tissue site 103, the tissue site 103 site may be treated with different processes to disrupt the debris 130. Examples of disruption can include softening of the debris 130, separation of the debris 130 from desired tissue, such as the subcutaneous tissue 115, preparation of the debris 130 for removal from the tissue site 103, and removal of the debris 130 from the tissue site 103.

The debris 130 can require debridement performed in an operating room. In some cases, tissue sites requiring debridement may not be life-threatening, and debridement may be considered low-priority. Low-priority cases can experience delays prior to treatment as other, more life-threatening, cases may be given priority for an operating room. As a result, low priority cases may need temporization. Temporization can include stasis of a tissue site, such as the tissue site 103, that limits deterioration of the tissue site prior to other treatments, such as debridement, negative-pressure therapy or instillation.

When debriding, clinicians may find it difficult to define separation between healthy, vital tissue and necrotic tissue. As a result, normal debridement techniques may remove too much healthy tissue or not enough necrotic tissue. If non-viable tissue demarcation does not extend deeper than the deep dermal layer, such as the dermis 109, or if the tissue site 103 is covered by the debris 130, such as slough or fibrin, gentle methods to remove the debris 130 should be considered to avoid excess damage to the tissue site 103

Debridement may include the removal of the debris 130. In some debridement processes, a mechanical process is used to remove the debris 130. Mechanical processes may include using scalpels or other cutting tools having a sharp edge to cut away the debris 130 from the tissue site. Other mechanical processes may use devices that can provide a stream of particles to impact the debris 130 to remove the debris 130 in an abrasion process, or jets of high pressure fluid to impact the debris 130 to remove the debris 130 using water-jet cutting or lavage. Typically, mechanical processes of debriding a tissue site may be painful and may require the application of local anesthetics. Mechanical processes also risk over removal of healthy tissue that can cause further damage to the tissue site 103 and delay the healing process.

Debridement may also be performed with an autolytic process. For example, an autolytic process may involve using enzymes and moisture produced by a tissue site to soften and liquefy the necrotic tissue and debris. Typically, a dressing may be placed over a tissue site having debris so that fluid produced by the tissue site may remain in place, hydrating the debris. Autolytic processes can be pain-free, but autolytic processes are a slow and can take many days. Because autolytic processes are slow, autolytic processes may also involve many dressing changes. Some autolytic processes may be paired with negative-pressure therapy so that, as debris hydrates, negative pressure supplied to a tissue site may draw off the debris. In some cases, a manifold positioned at a tissue site to distribute negative-pressure across the tissue site may become blocked or clogged with debris broken down by an autolytic process. If a manifold becomes clogged, negative-pressure may not be able to remove debris, which can slow or stop the autolytic process.

Debridement may also be performed by adding enzymes or other agents to the tissue site that digest tissue. Often, strict control of the placement of the enzymes and the length of time the enzymes are in contact with a tissue site must be maintained. If enzymes are left on a tissue site for longer than needed, the enzymes may remove too much healthy tissue, contaminate the tissue site, or be carried to other areas of a patient. Once carried to other areas of a patient, the enzymes may break down undamaged tissue and cause other complications.

These limitations and others may be addressed by the therapy system 100, which can provide negative-pressure therapy, instillation therapy, and disruption of debris. In some embodiments, the therapy system 100 can provide mechanical movement at a surface of the tissue site in combination with cyclic delivery and dwell of topical solutions to help solubilize debris. For example, a negative-pressure source may be fluidly coupled to a tissue site to provide negative pressure to the tissue site for negative-pressure therapy. In some embodiments, a fluid source may be fluidly coupled to a tissue site to provide therapeutic fluid to the tissue site for instillation therapy. In some embodiments, the therapy system 100 may include a contact layer positioned adjacent to a tissue site that may be used with negative-pressure therapy to disrupt areas of a tissue site having debris. In some embodiments, the therapy system 100 may include a contact layer positioned adjacent to a tissue site that may be used with instillation therapy to disrupt areas of a tissue site having debris. In some embodiments, the therapy system 100 may include a contact layer positioned adjacent to a tissue site that may be used with both negative-pressure therapy and instillation therapy to disrupt areas of a tissue site having debris. Following the disruption of the debris, negative-pressure therapy, instillation therapy, and other processes may be used to remove the debris from a tissue site. In some embodiments, the therapy system 100 may be used in conjunction with other tissue removal and debridement techniques. For example, the therapy system 100 may be used prior to enzymatic debridement to soften the debris. In another example, mechanical debridement may be used to remove a portion of the debris at the tissue site, and the therapy system 100 may then be used to remove the remaining debris while reducing the risk of trauma to the tissue site.

The therapy system 100 may be used on the tissue site 103 having the debris 130. In some embodiments, the contact layer 110 may be positioned adjacent to the tissue site 103 so that the contact layer 110 is in contact with the debris 130. In some embodiments, the retainer layer 108 may be positioned over the contact layer 110. In other embodiments, if the tissue site 103 has a depth that is about the same as a thickness 134 of the contact layer 110, the retainer layer 108 may not be used. In still other embodiments, the retainer layer 108 may be positioned over the contact layer 110, and if the depth of the tissue site 103 is greater than a thickness of the retainer layer 108 and the thickness 134 of the contact layer 110 combined, another retainer layer 108 may be placed over the contact layer 110 and the retainer layer 108.

In some embodiments, the contact layer 110 may have a substantially uniform thickness. The contact layer 110 may have the thickness 134. In some embodiments, the thickness 134 may be between about 7 mm and about 15 mm. In other embodiments, the thickness 134 may be thinner or thicker than the stated range as needed for the tissue site 103. In a preferred embodiment, the thickness 134 may be about 8 mm. In some embodiments, individual portions of the contact layer 110 may have a minimal tolerance from the thickness 134. In some embodiments, the thickness 134 may have a tolerance of about 2 mm. In some embodiments, the thickness 134 may be between about 6 mm and about 10 mm. The contact layer 110 may be flexible so that the contact layer 110 can be contoured to a surface of the tissue site 103.

In some embodiments, the contact layer 110 may be formed from thermoplastic elastomers (TPE), such as styrene ethylene butylene styrene (SEBS) copolymers, or thermoplastic polyurethane (TPU). The contact layer 110 may be formed by combining sheets of TPE or TPU. In some embodiments, the sheets of TPE or TPU may be bonded, welded, adhered, or otherwise coupled to one another. For example, in some embodiments, the sheets of TPE or TPU may be welded using radiant heat, radio-frequency welding, or laser welding. Supracor, Inc., Hexacor, Ltd., Hexcel Corp., and Econocorp, Inc. may produce suitable TPE or TPU sheets for the formation of the contact layer 110. In some embodiments, sheets of TPE or TPU having a thickness between about 0.2 mm and about 2.0 mm may be used to form a structure having the thickness 134. In some embodiments, the contact layer 110 may be formed from a 3D textile, also referred to as a spacer fabric. Suitable 3D textiles may be produced by Heathcoat Fabrics, Ltd., Baltex, and Mueller Textil Group. The contact layer 110 can also be formed from polyurethane, silicone, polyvinyl alcohol, and metals, such as copper, tin, silver or other beneficial metals.

In some embodiments, the contact layer 110 may be formed from a foam. For example, cellular foam, open-cell foam, reticulated foam, or porous tissue collections, may be used to form the contact layer 110. In some embodiments, the contact layer 110 may be formed of GranuFoam®, grey foam, or Zotefoam. Grey foam may be a polyester polyurethane foam having about 60 pores per inch (ppi). Zotefoam may be a closed-cell crosslinked polyolefin foam. In one non-limiting example, the contact layer 110 may be an open-cell, reticulated polyurethane foam such as GranuFoam® dressing available from Kinetic Concepts, Inc. of San Antonio, Texas; in other embodiments, the contact layer 110 may be an open-cell, reticulated polyurethane foam such as a V.A.C. VeraFlo® foam, also available from Kinetic Concepts, Inc., of San Antonio, Texas.

In some embodiments, the contact layer 110 may be formed from a foam that is mechanically or chemically compressed to increase the density of the foam at ambient pressure. A foam that is mechanically or chemically compressed may be referred to as a compressed foam. A compressed foam may be characterized by a firmness factor (FF) that is defined as a ratio of the density of a foam in a compressed state to the density of the same foam in an uncompressed state. For example, a firmness factor (FF) of 5 may refer to a compressed foam having a density that is five times greater than a density of the same foam in an uncompressed state. Mechanically or chemically compressing a foam may reduce a thickness of the foam at ambient pressure when compared to the same foam that has not been compressed. Reducing a thickness of a foam by mechanical or chemical compression may increase a density of the foam, which may increase the firmness factor (FF) of the foam. Increasing the firmness factor (FF) of a foam may increase a stiffness of the foam in a direction that is parallel to a thickness of the foam. For example, increasing a firmness factor (FF) of the contact layer 110 may increase a stiffness of the contact layer 110 in a direction that is parallel to the thickness 134 of the contact layer 110. In some embodiments, a compressed foam may be a compressed GranuFoam®. GranuFoam® may have a density of about 0.03 grams per centimeter$^3$ (g/cm$^3$) in its uncompressed state. If the GranuFoam® is compressed to have a firmness factor (FF) of 5, the GranuFoam® may be compressed until the density of the GranuFoam® is about 0.15 g/cm$^3$. V.A.C. VeraFlo® foam may also be compressed to form a compressed foam having a firmness factor (FF) up to 5. In some embodiments, the contact layer 110 may have a thickness between about 4 mm to about 15 mm, and more specifically, about 8 mm at ambient pressure. In an exemplary embodiment, if the thickness 134 of the contact layer is about 8 mm, and the contact layer 110 is positioned within the sealed therapeutic environment 128 and subjected to negative pressure of about −115 mmHg to about −135 mm Hg, the thickness 134 of the contact layer 110 may be between about 1 mm and about 5 mm and, generally, greater than about 3 mm.

A compressed foam may also be referred to as a felted foam. As with a compressed foam, a felted foam undergoes a thermoforming process to permanently compress the foam to increase the density of the foam. A felted foam may also be compared to other felted foams or compressed foams by comparing the firmness factor of the felted foam to the firmness factor of other compressed or uncompressed foams. Generally a compressed or felted foam may have a firmness factor greater than 1.

The firmness factor (FF) may also be used to compare compressed foam materials with non-foam materials. For example, a Supracor® material may have a firmness factor (FF) that allows Supracor® to be compared to compressed foams. In some embodiments, the firmness factor (FF) for a non-foam material may represent that the non-foam material has a stiffness that is equivalent to a stiffness of a compressed foam having the same firmness factor. For example, if a contact layer is formed from Supracor®, as illustrated in Table 1 below, the contact layer may have a stiffness that is about the same as the stiffness of a compressed GranuFoam® material having a firmness factor (FF) of 3.

Generally, if a compressed foam is subjected to negative pressure, the compressed foam exhibits less deformation than a similar uncompressed foam. If the contact layer 110 is formed of a compressed foam, the thickness 134 of the contact layer 110 may deform less than if the contact layer 110 is formed of a comparable uncompressed foam. The decrease in deformation may be caused by the increased stiffness as reflected by the firmness factor (FF). If subjected to the stress of negative pressure, the contact layer 110 that is formed of compressed foam may flatten less than the contact layer 110 that is formed from uncompressed foam. Consequently, if negative pressure is applied to the contact layer 110, the stiffness of the contact layer 110 in the direction parallel to the thickness 134 of the contact layer 110 allows the contact layer 110 to be more compliant or compressible in other directions, e.g., a direction perpendicular to the thickness 134. The foam material used to form a compressed foam may be either hydrophobic or hydrophilic. The foam material used to form a compressed foam may also be either reticulated or un-reticulated. The pore size of a foam material may vary according to needs of the contact layer 110 and the amount of compression of the foam. For example, in some embodiments, an uncompressed foam may have pore sizes in a range of about 400 microns to about 600 microns. If the same foam is compressed, the pore sizes may be smaller than when the foam is in its uncompressed state.

Figure 2:
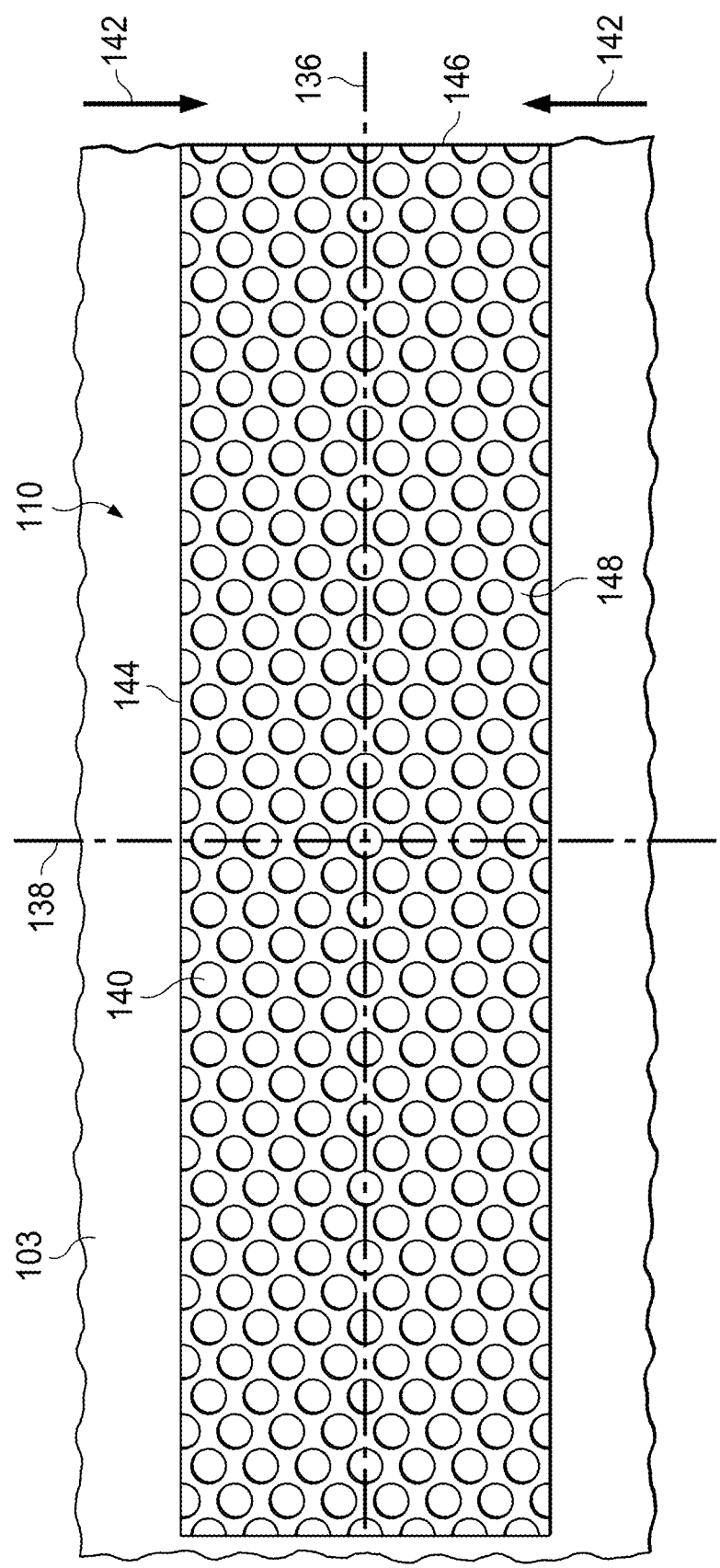
FIG. 2 is a plan view, illustrating details that may be associated with some embodiments of a contact layer of the therapy system of FIG. 1 in a first position.

FIG. 2 is a plan view, illustrating additional details that may be associated with some embodiments of the contact layer 110. The contact layer 110 may include a plurality of through-holes 140 or other perforations extending through the contact layer 110 to form walls 148. In some embodiments, an exterior surface of the walls 148 may be parallel to sides of the contact layer 110. In other embodiments, an interior surface of the walls 148 may be generally perpendicular to the tissue-facing surface 111 and the opposite surface 113 of the contact layer 110. Generally, the exterior surface or surfaces of the walls 148 may be coincident with the tissue-facing surface 111 and the opposite surface 113. The interior surface or surfaces of the walls 148 may form a perimeter 152 of each through-hole 140 and may connect the tissue facng surface 111 to the opposite surface 113. In some embodiments, the through-holes 140 may have a circular shape as shown. In some embodiments, the through-holes 140 may have diameters between about 5 mm and about 20 mm, and in some embodiments, the diameters of the through-holes 140 may be about 10 mm. The through-holes 140 may have a depth that is about equal to the thickness 134 of the contact layer 110. For example, the through-holes 140 may have a depth between about 6 mm to about 10 mm, and more specifically, about 8 mm at ambient pressure.

In some embodiments, the contact layer 110 may have a first orientation line 136 and a second orientation line 138 that is perpendicular to the first orientation line 136. The first orientation line 136 and the second orientation line 138 may be lines of symmetry of the contact layer 110. A line of symmetry may be, for example, an imaginary line across the tissue-facing surface 111 or the opposite surface 113 of the contact layer 110 defining a fold line such that if the contact layer 110 is folded on the line of symmetry, the through-holes 140 and walls 148 would be coincidentally aligned. Generally, the first orientation line 136 and the second orientation line 138 aid in the description of the contact layer 110. In some embodiments, the first orientation line 136 and the second orientation line 138 may be used to refer to the desired directions of contraction of the contact layer 110. For example, the desired direction of contraction may be parallel to the second orientation line 138 and perpendicular to the first orientation line 136. In other embodiments, the desired direction of contraction may be parallel to the first orientation line 136 and perpendicular to the second orientation line 138. In still other embodiments, the desired direction of contraction may be at a non-perpendicular angle to both the first orientation line 136 and the second orientation line 138. In other embodiments, the contact layer 110 may not have a desired direction of contraction. Generally, the contact layer 110 may be placed at the tissue site 103 so that the second orientation line 138 extends across the debris 130 of FIG. 1. Although the contact layer 110 is shown as having a generally rectangular shape including longitudinal edges 144 and latitudinal edges 146, the contact layer 110 may have other shapes. For example, the contact layer 110 may have a diamond, square, or circular shape. In some embodiments, the shape of the contact layer 110 may be selected to accommodate the type of tissue site being treated. For example, the contact layer 110 may have an oval or circular shape to accommodate an oval or circular tissue site. In some embodiments, the first orientation line 136 may be parallel to the longitudinal edges 144.

Figure 3:
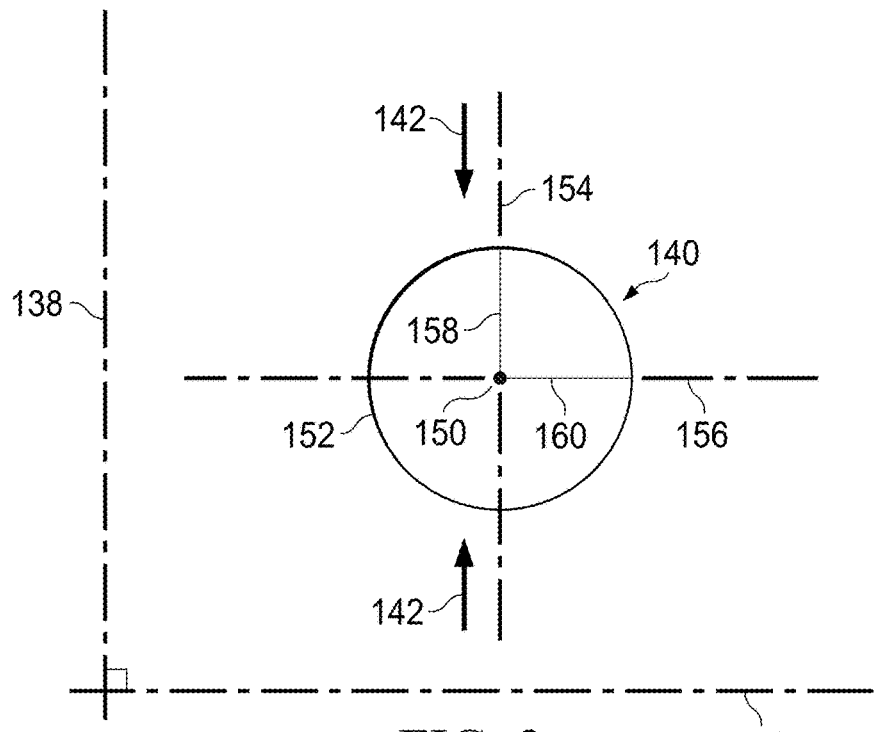
FIG. 3 is a schematic view, illustrating details that may be associated with some embodiments of a through-hole of the contact layer of FIG. 2.

Referring more specifically to FIG. 3, a single through-hole 140 having a circular shape is shown. The through-hole 140 may include a center 150 and a perimeter 152. The through-hole 140 may have a perforation shape factor (PSF). The perforation shape factor (PSF) may represent an orientation of the through-hole 140 relative to the first orientation line 136 and the second orientation line 138. Generally, the perforation shape factor (PSF) is a ratio of ½ a maximum length of the through-hole 140 that is parallel to the desired direction of contraction to ½ a maximum length of the through-hole 140 that is perpendicular to the desired direction of contraction. For descriptive purposes, the desired direction of contraction is parallel to the second orientation line 138. The desired direction of contraction may be indicated by a lateral force 142. For reference, the through-hole 140 may have an X-axis 156 extending through the center 150 between opposing vertices of the hexagon and parallel to the first orientation line 136, and a Y-axis 154 extending through the center 150 between opposing sides of the hexagon and parallel to the second orientation line 138. The perforation shape factor (PSF) of the through-hole 140 may be defined as a ratio of a line segment 158 on the Y-axis 154 extending from the center 150 to the perimeter 152 of the through-hole 140, to a line segment 160 on the X-axis 156 extending from the center 150 to the perimeter 152 of the through-hole 140. If a length of the line segment 158 is 2.5 mm and the length of the line segment 160 is 2.5 mm, the perforation shape factor (PSF) would be 1. In other embodiments, the through-holes 140 may have other shapes and orientations, for example, oval, hexagonal, square, triangular, or amorphous or irregular and be oriented relative to the first orientation line 136 and the second orientation line 138 so that the perforation shape factor (PSF) may range from about 0.5 to about 1.10.

Figure 4:
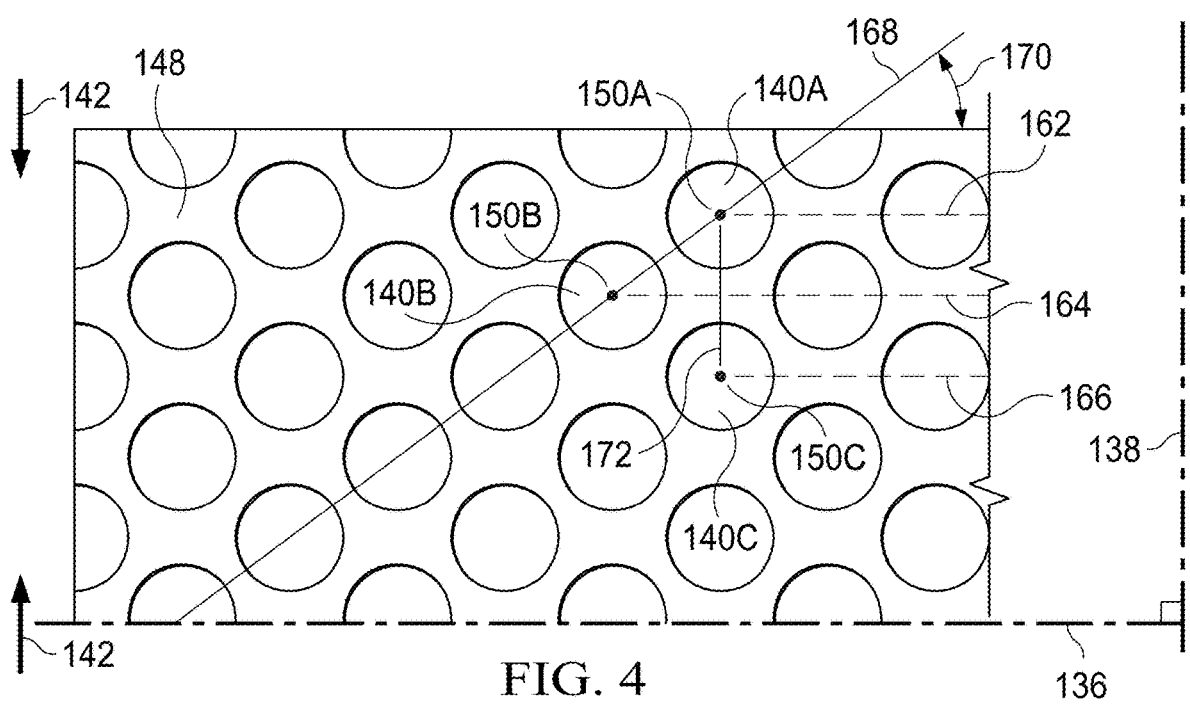
FIG. 4 is a plan view, illustrating details that may be associated with some embodiments of the through-holes of the contact layer of FIG. 2.

Referring to FIG. 4, a portion of the contact layer 110 of FIG. 1 is shown. The contact layer 110 may include the plurality of through-holes 140 aligned in parallel rows to form an array. The array of through-holes 140 may include a first row 162 of the through-holes 140, a second row 164 of the through-holes 140, and a third row 166 of the through-holes 140. In some embodiments, a width of the wall 148 between the perimeters 152 of adjacent the through-holes 140 in a row, such as the first row 162, may be about 5 mm. The centers 150 of the through-holes 140 in adjacent rows, for example, the first row 162 and the second row 164, may be characterized by being offset from the second orientation line 138 along the first orientation line 136. In some embodiments, a line connecting the centers of adjacent rows may form a strut angle (SA) with the first orientation line 136. For example, a first through-hole 140A in the first row 162 may have a center 150A, and a second through-hole 140B in the second row 164 may have a center 150B. A strut line 168 may connect the center 150A with the center 150B. The strut line 168 may form an angle 170 with the first orientation line 136. The angle 170 may be the strut angle (SA) of the contact layer 110. In some embodiments, the strut angle (SA) may be less than about 90°. In other embodiments, the strut angle (SA) may be between about 30° and about 70° relative to the first orientation line 136. In other embodiments, the strut angle (SA) may be about 66° from the first orientation line 136. Generally, as the strut angle (SA) decreases, a stiffness of the contact layer 110 in a direction parallel to the first orientation line 136 may increase. Increasing the stiffness of the contact layer 110 parallel to the first orientation line 136 may increase the compressibility of the contact layer 110 perpendicular to the first orientation line 136. Consequently, if negative pressure is applied to the contact layer 110, the contact layer 110 may be more compliant or compressible in a direction perpendicular to the first orientation line 136. By increasing the compressibility of the contact layer 110 in a direction perpendicular to the first orientation line 136, the contact layer 110 may collapse to apply the lateral force 142 to the tissue site 103 described in more detail below.

In some embodiments, the centers 150 of the through-holes 140 in alternating rows, for example, the center 150A of the first through-hole 140A in the first row 162 and a center 150C of a through-hole 140C in the third row 166, may be spaced from each other parallel to the second orientation line 138 by a length 172. In some embodiments, the length 172 may be greater than an effective diameter of the through-hole 140. If the centers 150 of through-holes 140 in alternating rows are separated by the length 172, the exterior surface of the walls 148 parallel to the first orientation line 136 may be considered continuous. Generally, exterior surface of the walls 148 may be continuous if the exterior surface of the walls 148 do not have any discontinuities or breaks between through-holes 140. In some embodiments, the length 172 may be between about 7 mm and about 25 mm.

Regardless of the shape of the through-holes 140, the through-holes 140 in the contact layer 110 may leave void spaces in the contact layer 110 and on the tissue-facing surface 111 and the opposite surface 113 of the contact layer 110 so that only the exterior surface of the walls 148 of the contact layer 110 remain with a surface available to contact the tissue site 103. It may be desirable to minimize the exterior surface of the walls 148 so that the through-holes 140 may collapse, causing the contact layer 110 to collapse and generate the lateral force 142 in a direction perpendicular to the first orientation line 136. However, it may also be desirable not to minimize the exterior surface of the walls 148 so much that the contact layer 110 becomes too fragile for sustaining the application of a negative pressure. The void space percentage (VS) of the through-holes 140 may be equal to the percentage of the volume or surface area of the void spaces of the tissue-facing surface 111 created by the through-holes 140 to the total volume or surface area of the tissue-facing surface 111 of the contact layer 110. In some embodiments, the void space percentage (VS) may be between about 40% and about 75%. In other embodiments, the void space percentage (VS) may be about 55%. The organization of the through-holes 140 can also impact the void space percentage (VS), influencing the total surface area of the contact layer 110 that may contact the tissue site 103. In some embodiments, the longitudinal edge 144 and the latitudinal edge 146 of the contact layer 110 may be discontinuous. An edge may be discontinuous where the through-holes 140 overlap an edge causing the edge to have a non-linear profile. A discontinuous edge may reduce the disruption of keratinocyte migration and enhance re-epithelialization while negative pressure is applied to the dressing 102.

In other embodiments, the through-holes 140 of the contact layer 110 may have a depth that is less than the thickness 134 of the contact layer 110. For example, the holes 140 may be blind holes formed in the tissue-facing surface 111 of the contact layer 110. The holes 140 may leave void spaces in the contact layer 110 on the tissue-facing surface 111 so that only the exterior surface of the walls 148 of the contact layer 110 on the tissue-facing surface 111 remain with a surface available to contact the tissue site 103 at ambient pressure. If a depth of the holes 140 extending from the tissue-facing surface 111 toward the opposite surface 113 is less than the thickness 134, the void space percentage (VS) of the opposite surface 113 may be zero, while the void space percentage (VS) of the tissue-facing surface 111 is greater than zero, for example 55%. As used herein, the holes 140 may be similar to and operate as described with respect to the through-holes 140, having similar structural, positional, and operational properties.

In some embodiments, the through-holes 140 may be formed during molding of the contact layer 110. In other embodiments, the through-holes 140 may be formed by cutting, melting, drilling, or vaporizing the contact layer 110 after the contact layer 110 is formed. For example, the through-holes 140 may be formed in the contact layer 110 by laser cutting the compressed foam of the contact layer 110. In some embodiments, the through-holes 140 may be formed so that the interior surfaces of the walls 148 of the through-holes 140 are parallel to the thickness 134. In other embodiments, the through-holes 140 may be formed so that the interior surfaces of the walls 148 of the through-holes 140 form a non-perpendicular angle with the tissue-facing surface 111. In still other embodiments, the interior surfaces of the walls 148 of the through-holes 140 may taper toward the center 150 of the through-holes 140 to form conical, pyramidal, or other irregular through-hole shapes. If the interior surfaces of the walls 148 of the through-holes 140 taper, the through-holes 140 may have a height less than the thickness 134 of the contact layer 110.

In some embodiments, formation of the through-holes 140 may thermoform the material of the contact layer 110, for example a compressed foam or a felted foam, causing the interior surface of the walls 148 extending between the tissue-facing surface 111 and the opposite surface 113 to be smooth. As used herein, smoothness may refer to the formation of the through-holes 140 that causes the interior surface of the walls 148 that extends between the tissue-facing surface 111 and the opposite surface 113 to be substantially free of pores if compared to an uncut portion of the contact layer 110. For example, laser-cutting the through-holes 140 into the contact layer 110, may plastically deform the material of the contact layer 110, closing any pores on the interior surfaces of the walls 148 that extend between the tissue-facing surface 111 and the opposite surface 113. In some embodiments, a smooth interior surface of the walls 148 may limit or otherwise inhibit ingrowth of tissue into the contact layer 110 through the through-holes 140. In other embodiments, the smooth interior surfaces of the walls 148 may be formed by a smooth material or a smooth coating.

In some embodiments, an effective diameter of the through-holes 140 may be selected to permit flow of particulates through the through-holes 140. In some embodiments, the diameter of the through-holes 140 may be selected based on the size of the solubilized debris to be lifted from the tissue site 103. Larger through-holes 140 may allow larger debris to pass through the contact layer 110, and smaller through-holes 140 may allow smaller debris to pass through the contact layer 110 while blocking debris larger than the through-holes. In some embodiments, successive applications of the dressing 102 can use contact layers 110 having successively smaller diameters of the through-holes 140 as the size of the solubilized debris in the tissue site 103 decreases. Sequentially decreasing diameters of the through-holes 140 may also aid in fine tuning a level of tissue disruption to the debris 130 during the treatment of the tissue site 103. The diameter of the through-holes 140 can also influence fluid movement in the contact layer 110 and the dressing 102. For example, the contact layer 110 can channel fluid in the dressing 102 toward the through-holes 140 to aid in the disruption of the debris 130 on the tissue site 103. Variation of the diameters of the through-holes 140 can vary how fluid is moved through the dressing 102 with respect to both the removal of fluid and the application of negative pressure. In some embodiments, the diameter of the through-holes 140 is between about 5 mm and about 20 mm and, more specifically, about 10 mm.

An effective diameter of a non-circular area is defined as a diameter of a circular area having the same surface area as the non-circular area. In some embodiments, each through-hole 140 may have an effective diameter of about 3.5 mm. In other embodiments, each through-hole 140 may have an effective diameter between about 5 mm and about 20 mm. The effective diameter of the through-holes 140 should be distinguished from the porosity of the material forming the walls 148 of the contact layer 110. Generally, an effective diameter of the through-holes 140 is an order of magnitude larger than the effective diameter of the pores of a material forming the contact layer 110. For example, the effective diameter of the through-holes 140 may be larger than about 1 mm, while the walls 148 may be formed from GranuFoam® material having a pore size less than about 600 microns. In some embodiments, the pores of the walls 148 may not create openings that extend all the way through the material. Generally, the through-holes 140 do not include pores formed by the foam formation process, and the through-holes 140 may have an average effective diameter that is greater than ten times an average effective diameter of pores of a material.

Referring now to both FIGS. 2 and 4, the through-holes 140 may form a pattern depending on the geometry of the through-holes 140 and the alignment of the through-holes 140 between adjacent and alternating rows in the contact layer 110 with respect to the first orientation line 136. If the contact layer 110 is subjected to negative pressure, the through-holes 140 of the contact layer 110 may contract. As used herein, contraction can refer to both vertical compression of a body parallel to a thickness of the body, such as the contact layer 110, and lateral compression of a body perpendicular to a thickness of the body, such as the contact layer 110. In some embodiments the void space percentage (VS), the perforation shape factor (PSF), and the strut angle (SA) may cause the contact layer 110 to contract along the second orientation line 138 perpendicular to the first orientation line 136 as shown in more detail in FIG. 5. If the contact layer 110 is positioned on the tissue site 103, the contact layer 110 may generate the lateral force 142 along the second orientation line 138, contracting the contact layer 110, as shown in more detail in FIG. 5. The lateral force 142 may be optimized by adjusting the factors described above as set forth in Table 1 below. In some embodiments, the through-holes 140 may be circular, have a strut angle (SA) of approximately 37°, a void space percentage (VS) of about 54%, a firmness factor (FF) of about 5, a perforation shape factor (PSF) of about 1, and a diameter of about 5 mm. If the contact layer 110 is subjected to a negative pressure of about −125 mmHg, the contact layer 110 asserts the lateral force 142 of approximately 11.9 N. If the diameter of the through-holes 140 of the contact layer 110 is increased to about 20 mm, the void space percentage (VS) changed to about 52%, the strut angle (SA) changed to about 52°, and the perforation shape factor (PSF) and the firmness factor (FF) remain the same, the lateral force 142 is decreased to about 6.5 N. In other embodiments, the through-holes 140 may be hexagonal, have a strut angle (SA) of approximately 66°, a void space percentage (VS) of about 55%, a firmness factor (FF) of about 5, a perforation shape factor (PSF) of about 1.07, and an effective diameter of about 5 mm. If the contact layer 110 is subjected to a negative pressure of about −125 mmHg, the lateral force 142 asserted by the contact layer 110 is about 13.3 N. If the effective diameter of the through-holes 140 of the contact layer 110 is increased to 10 mm, the lateral force 142 is decreased to about 7.5 N.

Figure 5:
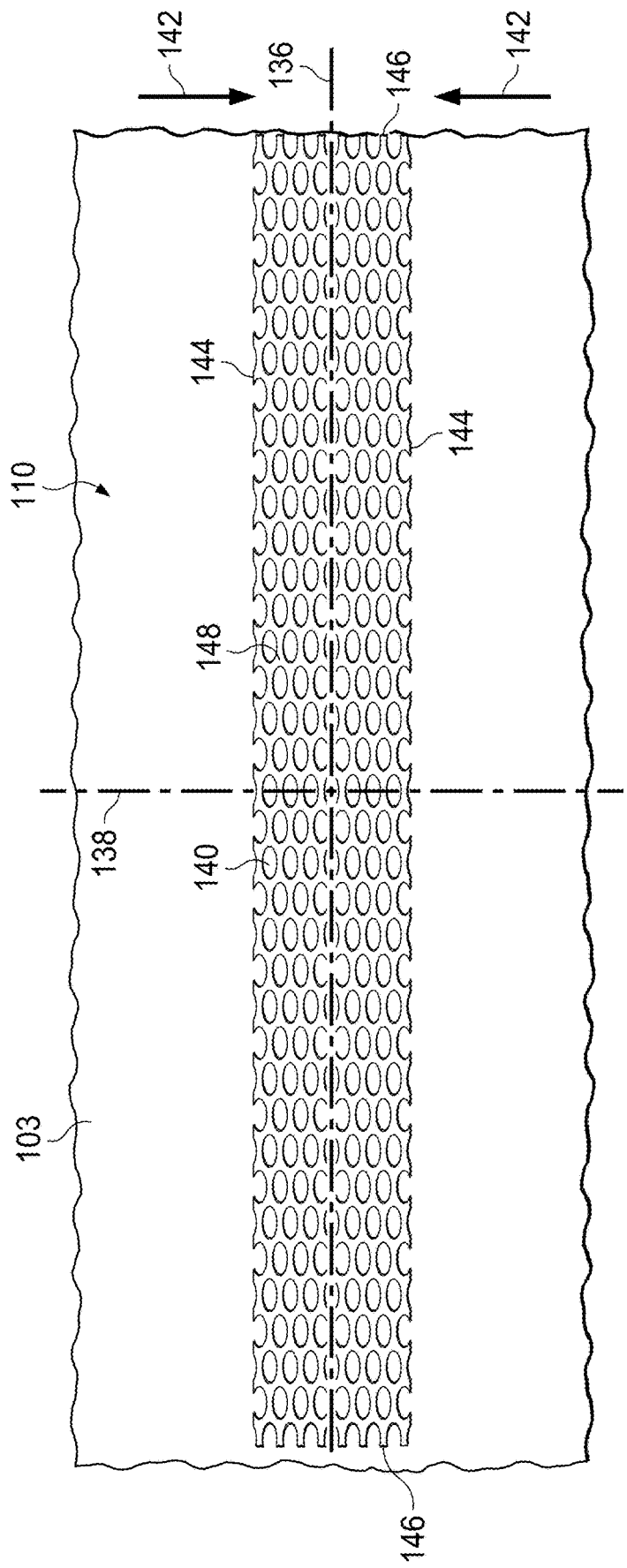
FIG. 5 is a plan view, illustrating details that may be associated with some embodiments of the contact layer of FIG. 2 in a second position.

Referring to FIG. 5, the contact layer 110 is in the second position, or contracted position, as indicated by the lateral force 142. In operation, negative pressure is supplied to the sealed therapeutic environment 128 with the negative-pressure source 104. In response to the supply of negative pressure, the contact layer 110 contracts from the relaxed position illustrated in FIG. 2 to the contracted position illustrated in FIG. 5. In one embodiment, the thickness 134 of the contact layer 110 remains substantially the same. When the negative pressure is removed, for example, by venting the negative pressure, the contact layer 110 expands back to the relaxed position. If the contact layer 110 is cycled between the contracted and relaxed positions of FIG. 5 and FIG. 2, respectively, the tissue-facing surface 111 of the contact layer 110 may disrupt the debris 130 on the tissue site 103 by rubbing the debris 130 from the tissue site 103. The edges of the through-holes 140 formed by the tissue-facing surface 111 and the interior surfaces or transverse surfaces of the walls 148 can form cutting edges that can disrupt the debris 130 in the tissue site 103, allowing the debris 130 to exit through the through-holes 140. In some embodiments, the cutting edges are defined by the perimeter 152 where each through-hole 140 intersects the tissue-facing surface 111.

In some embodiments, the material, the void space percentage (VS), the firmness factor, the strut angle, the hole shape, the perforation shape factor (PSF), and the hole diameter may be selected to increase compression or collapse of the contact layer 110 in a lateral direction, as shown by the lateral force 142, by forming weaker walls 148. Conversely, the factors may be selected to decrease compression or collapse of the contact layer 110 in a lateral direction, as shown by the lateral force 142, by forming stronger walls 148. Similarly, the factors described herein can be selected to decrease or increase the compression or collapse of the contact layer 110 perpendicular to the lateral force 142.

In some embodiments, the therapy system 100 may provide cyclic therapy. Cyclic therapy may alternately apply negative pressure to and vent negative pressure from the sealed therapeutic environment 128. In some embodiments, negative pressure may be supplied to the sealed therapeutic environment 128 until the pressure in the sealed therapeutic environment 128 reaches a predetermined therapy pressure. If negative pressure is supplied to the sealed therapeutic environment 128, the debris 130 and the subcutaneous tissue 115 may be drawn into the through-holes 140. In some embodiments, the sealed therapeutic environment 128 may remain at the therapy pressure for a predetermined therapy period such as, for example, about 10 minutes. In other embodiments, the therapy period may be longer or shorter as needed to supply appropriate negative-pressure therapy to the tissue site 103.

Following the therapy period, the sealed therapeutic environment 128 may be vented. For example, the negative-pressure source 104 may fluidly couple the sealed therapeutic environment 128 to the atmosphere (not shown), allowing the sealed therapeutic environment 128 to return to ambient pressure. In some embodiments, the negative-pressure source 104 may vent the sealed therapeutic environment 128 for about 1 minute. In other embodiments, the negative-pressure source 104 may vent the sealed therapeutic environment 128 for longer or shorter periods. After venting of the sealed therapeutic environment 128, the negative-pressure source 104 may be operated to begin another negative-pressure therapy cycle.

In some embodiments, instillation therapy may be combined with negative-pressure therapy. For example, following the therapy period of negative-pressure therapy, the fluid source 120 may operate to provide fluid to the sealed therapeutic environment 128. In some embodiments, the fluid source 120 may provide fluid while the negative-pressure source 104 vents the sealed therapeutic environment 128. For example, the fluid source 120 may include a pump configured to move instillation fluid from the fluid source 120 to the sealed therapeutic environment 128. In some embodiments, the fluid source 120 may not have a pump and may operate using a gravity feed system. In other embodiments, the negative-pressure source 104 may not vent the sealed therapeutic environment 128. Instead, the negative pressure in the sealed therapeutic environment 128 is used to draw instillation fluid from the fluid source 120 into the sealed therapeutic environment 128.

In some embodiments, the fluid source 120 may provide a volume of fluid to the sealed therapeutic environment 128. In some embodiments, the volume of fluid may be the same as a volume of the sealed therapeutic environment 128. In other embodiments, the volume of fluid may be smaller or larger than the sealed therapeutic environment 128 as needed to appropriately apply instillation therapy. Instilling of the tissue site 103 may raise a pressure in the sealed therapeutic environment 128 to a pressure greater than the ambient pressure, for example to between about 0 mmHg and about 15 mmHg and, more specifically, about 5 mmHg. In some embodiments, the fluid provided by the fluid source 120 may remain in the sealed therapeutic environment 128 for a dwell time. In some embodiments, the dwell time is about 5 minutes. In other embodiments, the dwell time may be longer or shorter as needed to appropriately administer instillation therapy to the tissue site 103. For example, the dwell time may be zero.

At the conclusion of the dwell time, the negative-pressure source 104 may be operated to draw the instillation fluid into the container 112, completing a cycle of therapy. As the instillation fluid is removed from the sealed therapeutic environment 128 with negative pressure, negative pressure may also be supplied to the sealed therapeutic environment 128, starting another cycle of therapy.

Figure 6:
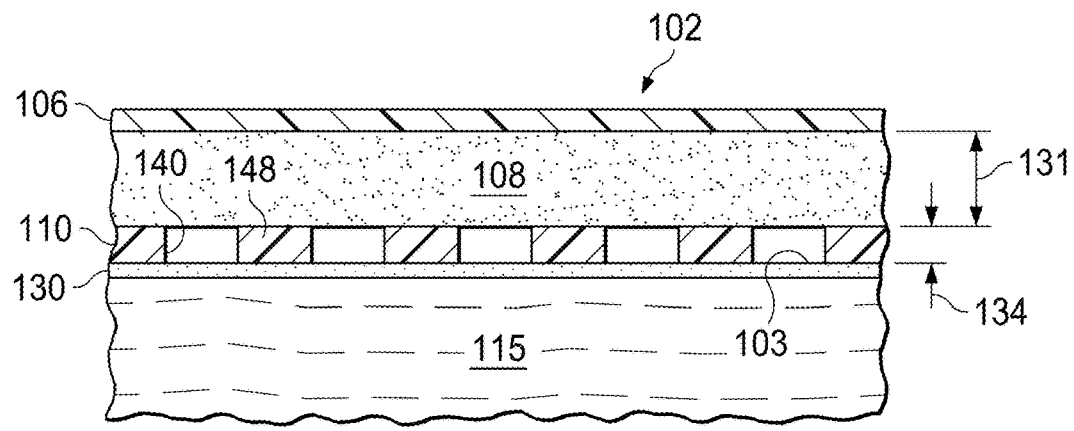
FIG. 6 is a sectional view, illustrating details that may be associated with some embodiments of the contact layer of FIG. 2 at ambient pressure.

FIG. 6 is a sectional view of a portion of the contact layer 110, illustrating additional details that may be associated with some embodiments. The contact layer 110 and the retainer layer 108 may be placed at the tissue site 103 having the debris 130 covering the subcutaneous tissue 115. The drape 106 may be placed over the retainer layer 108 to provide the sealed therapeutic environment 128 for the application of negative pressure therapy or instillation therapy. As shown in FIG. 6, the retainer layer 108 may have a thickness 131 if the pressure in the sealed therapeutic environment 128 is about an ambient pressure. In some embodiments, the thickness 131 may be about 8 mm. In other embodiments, the thickness 131 may be about 16 mm.

Figure 7:
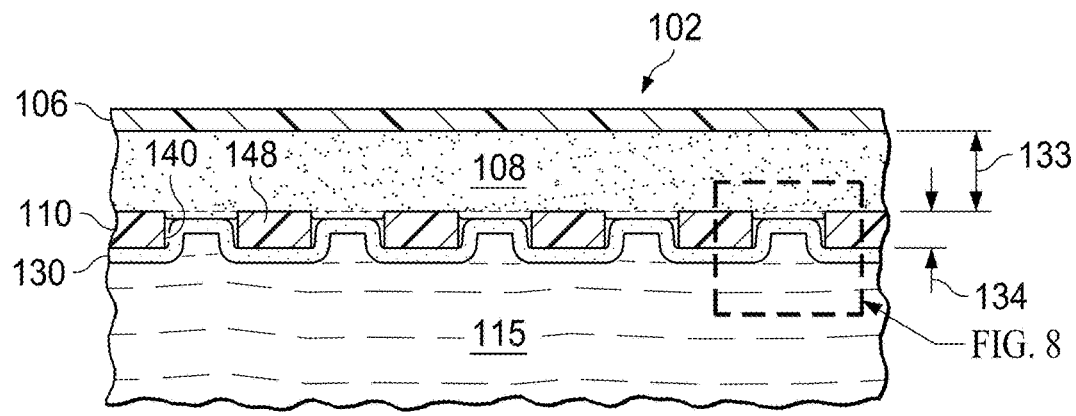
FIG. 7 is a sectional view, illustrating details that may be associated with some embodiments of the contact layer of FIG. 2 during negative-pressure therapy.

FIG. 7 is a sectional view of a portion of the dressing 102 during negative-pressure therapy, illustrating additional details that may be associated with some embodiments. For example, FIG. 7 may illustrate a moment in time where a pressure in the sealed therapeutic environment 128 may be about 125 mmHg of negative pressure. In some embodiments, the retainer layer 108 may be an non-precompressed foam, and the contact layer 110 may be a precompressed foam. In response to the application of negative pressure, the contact layer 110 may not compress, and the retainer layer 108 may compress so that the manifold has a thickness 133. In some embodiments, the thickness 133 of the retainer layer 108 during negative-pressure therapy may be less than the thickness 131 of the retainer layer 108 if the pressure in the sealed therapeutic environment 128 is about the ambient pressure.

In some embodiments, negative pressure in the sealed therapeutic environment 128 can generate concentrated stresses in the retainer layer 108 adjacent to the through-holes 140 in the contact layer 110. The concentrated stresses can cause macro-deformation of the retainer layer 108 that draws portions of the retainer layer 108 into the through-holes 140 of the contact layer 110. Similarly, negative pressure in the sealed therapeutic environment 128 can generate concentrated stresses in the debris 130 adjacent to the through-holes 140 in the contact layer 110. The concentrated stresses can cause macro-deformations of the debris 130 and the subcutaneous tissue 115 that draws portions of the debris 130 and the subcutaneous tissue 115 into the through-holes 140.

Figure 8:
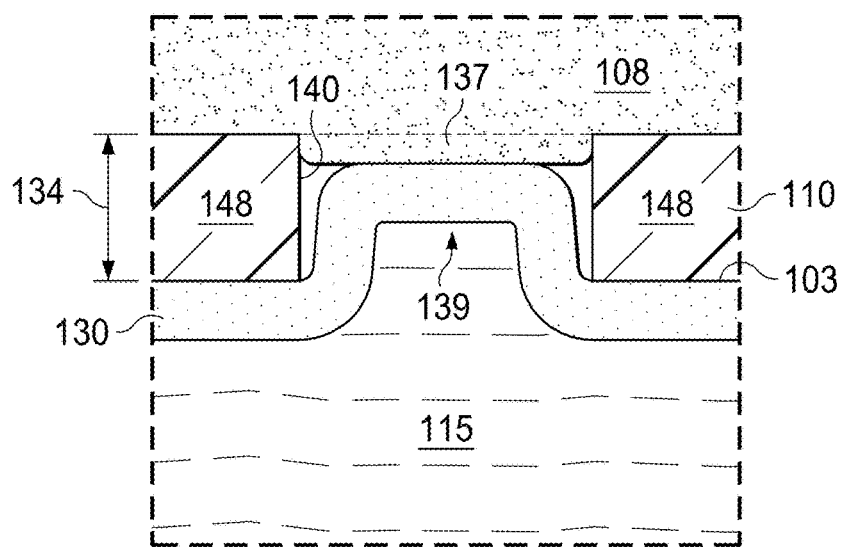
FIG. 8 is a sectional detail view of FIG. 7, illustrating details that may be associated with some embodiments of the contact layer of FIG. 2 during negative-pressure therapy.

FIG. 8 is a detail view of the contact layer 110, illustrating additional details of the operation of the contact layer 110 during negative-pressure therapy. Portions of the retainer layer 108 in contact with the opposite surface 113 of the contact layer 110 may be drawn into the through-holes 140 to form bosses 137. The bosses 137 may have a shape that corresponds to the through-holes 140. A height of the bosses 137 from the retainer layer 108 may be dependent on the pressure of the negative pressure in the sealed therapeutic environment 128, the area of the through-holes 140, and the firmness factor of the retainer layer 108.

Similarly, the through-holes 140 of the contact layer 110 may create macro-pressure points in portions of the debris 130 and the subcutaneous tissue 115 that are in contact with the tissue-facing surface 111 of the contact layer 110, causing tissue puckering and nodules 139 in the debris 130 and the subcutaneous tissue 115.

A height of the nodules 139 over the surrounding tissue may be selected to maximize disruption of debris 130 and minimize damage to subcutaneous tissue 115 or other desired tissue. Generally, the pressure in the sealed therapeutic environment 128 can exert a force that is proportional to the area over which the pressure is applied. At the through-holes 140 of the contact layer 110, the force may be concentrated as the resistance to the application of the pressure is less than in the walls 148 of the contact layer 110. In response to the force generated by the pressure at the through-holes 140, the debris 130 and the subcutaneous tissue 115 that forms the nodules 139 may be drawn into and through the through-holes 140 until the force applied by the pressure is equalized by the reactive force of the debris 130 and the subcutaneous tissue 115. In some embodiments where the negative pressure in the sealed therapeutic environment 128 may cause tearing, the thickness 134 of the contact layer 110 may be selected to limit the height of the nodules 139 over the surrounding tissue. In some embodiments, the retainer layer 108 may limit the height of the nodules 139 to the thickness 134 of the contact layer 110 under negative pressure if the contact layer is compressible. In other embodiments, the bosses 137 of the retainer layer 108 may limit the height of the nodules 139 to a height that is less than the thickness 134 of the contact layer 110. By controlling the firmness factor of the retainer layer 108, the height of the bosses 137 over the surrounding material of the retainer layer 108 can be controlled. The height of the nodules 139 can be limited to the difference of the thickness 134 of the contact layer 110 and the height of the bosses 137. In some embodiments, the height of the bosses 137 can vary from zero to several millimeters as the firmness factor of the retainer layer 108 decreases. In an exemplary embodiment, the thickness 134 of the contact layer 110 may be about 7 mm. During the application of negative pressure, the bosses 137 may have a height between about 4 mm to about 5 mm, limiting the height of the nodules to about 2 mm to about 3 mm. By controlling the height of the nodules 139 by controlling the thickness 134 of the contact layer 110, the firmness factor of the retainer layer 108, or both, the aggressiveness of disruption to the debris 130 and tearing can be controlled.

In some embodiments, the height of the nodules 139 can also be controlled by controlling an expected compression of the contact layer 110 during negative-pressure therapy. For example, the contact layer 110 may have a thickness 134 of about 8 mm. If the contact layer 110 is formed from a compressed foam, the firmness factor of the contact layer 110 may be higher; however, the contact layer 110 may still reduce in thickness in response to negative pressure in the sealed therapeutic environment 128. In one embodiment, application of negative pressure of between about −50 mmHg and about −350 mmHg, between about −100 mm Hg and about −250 mmHg and, more specifically, about −125 mmHg in the sealed therapeutic environment 128 may reduce the thickness 134 of the contact layer 110 from about 8 mm to about 3 mm. If the retainer layer 108 is placed over the contact layer 110, the height of the nodules 139 may be limited to be no greater than the thickness 134 of the contact layer 110 during negative-pressure therapy, for example, about 3 mm. By controlling the height of the nodules 139, the forces applied to the debris 130 by the contact layer 110 can be adjusted and the degree that the debris 130 is stretched can be varied.

In some embodiments, the formation of the bosses 137 and the nodules 139 can cause the debris 130 to remain in contact with a tissue interface 107 during negative pressure therapy. For example, the nodules 139 may contact the sidewalls of the through-holes 140 of the contact layer 110 and the bosses 137 of the retainer layer 108, while the surrounding tissue may contact the tissue-facing surface 111 of the contact layer 110. In some embodiments, formation of the nodules 139 may lift debris and particulates off of the surrounding tissue, operating in a piston-like manner to move debris toward the retainer layer 108 and out of the sealed therapeutic environment 128.

In response to the return of the sealed therapeutic environment 128 to ambient pressure by venting the sealed therapeutic environment 128, the debris 130 and the subcutaneous tissue 115 may leave the through-holes 140, returning to the position shown in FIG. 6.

Figure 9:
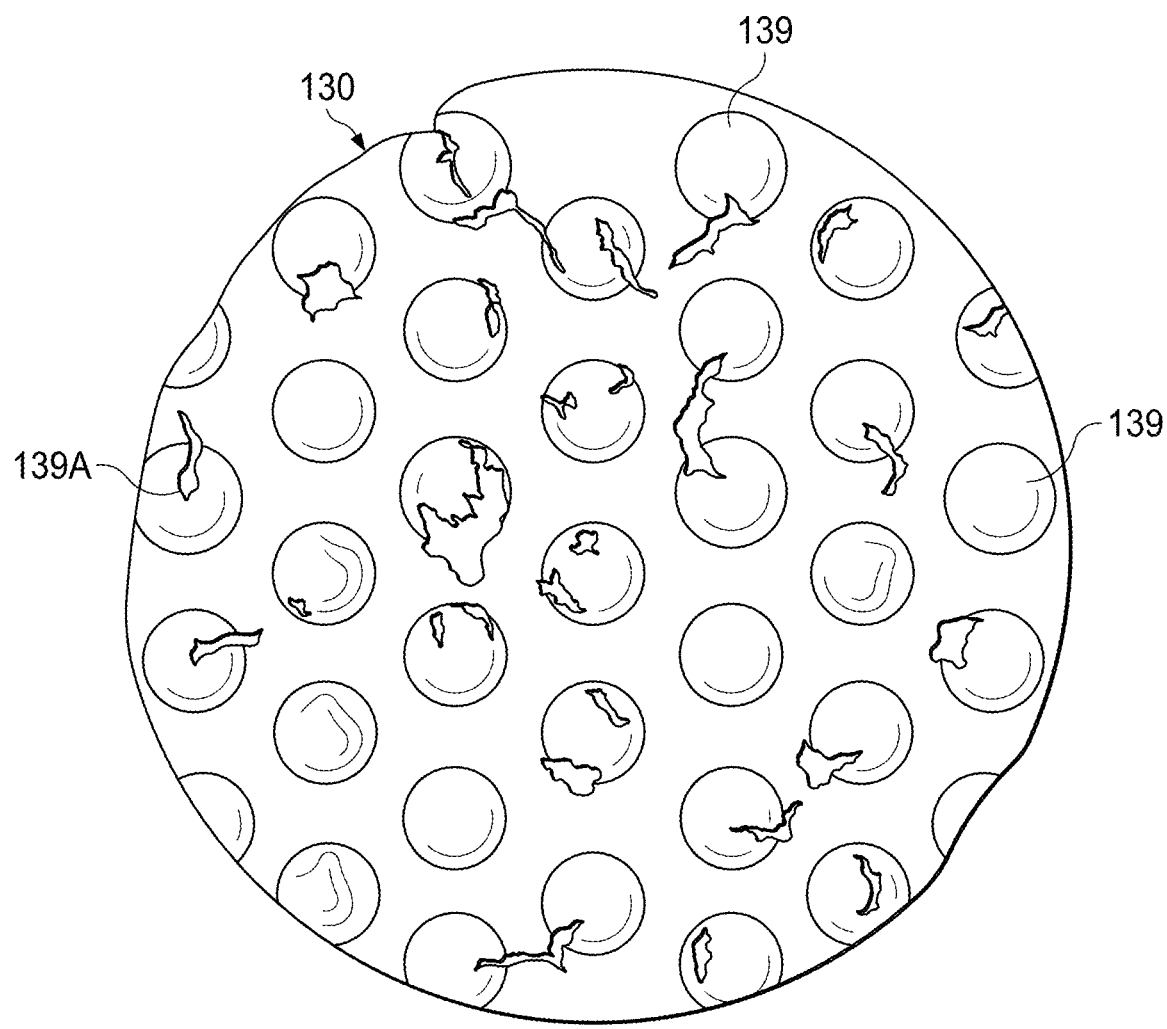
FIG. 9 is a plan view, illustrating details that may be associated with treatment using the contact layer of FIG. 2.

The application and removal of negative pressure to the sealed therapeutic environment 128 can disrupt the debris 130. For example, FIG. 9 is a top view of the debris 130, illustrating additional details that may be associated with some embodiments. As shown in FIG. 9, the nodules 139 may rupture. For example, the debris 130 in a nodule 139A may rupture, aiding in the removal of the debris 130. In some embodiments, repeated application of negative-pressure therapy and instillation therapy while the contact layer 110 is disposed over the debris 130 may disrupt the debris 130, allowing the debris 130 to be removed during dressing changes. In other embodiments, the contact layer 110 may disrupt the debris 130 so that the debris 130 can be removed by negative pressure. In still other embodiments, the contact layer 110 may disrupt the debris 130, aiding removal of the debris 130 during debridement processes.

With each cycle of therapy, the contact layer 110 may form nodules 139 in the debris 130. The formation of the nodules 139 and release of the nodules 139 by the contact layer 110 during therapy may disrupt the debris 130. With each subsequent cycle of therapy, disruption of the debris 130 can be increased.

Disruption of the debris 130 can be caused, at least in part, by the concentrated forces applied to the debris 130 by the through-holes 140 and the walls 148 of the contact layer 110. The forces applied to the debris 130 can be a function of the negative pressure supplied to the sealed therapeutic environment 128 and the area of each through-hole 140. For example, if the negative pressure supplied to the sealed therapeutic environment 128 is about 125 mmHg and the diameter of each through-hole 140 is about 5 mm, the force applied at each through-hole 140 is about 0.07 lbs. If the diameter of each through-hole 140 is increased to about 8 mm, the force applied at each through-hole 140 can increase up to 6 times. Generally, the relationship between the diameter of each through-hole 140 and the applied force at each through-hole 140 is not linear and can increase exponentially with an increase in diameter.

In some embodiments, the negative pressure applied by the negative-pressure source 104 may be cycled rapidly. For example, negative pressure may be supplied for a few seconds, then vented for a few seconds, causing a pulsation of negative pressure in the sealed therapeutic environment 128. The pulsation of the negative pressure can pulsate the nodules 139, causing further disruption of the debris 130.

In some embodiments, the cyclical application of instillation therapy and negative pressure therapy may cause micro-floating. For example, negative pressure may be applied to the sealed therapeutic environment 128 during a negative-pressure therapy cycle. Following the conclusion of the negative-pressure therapy cycle, instillation fluid may be supplied during the instillation therapy cycle. The instillation fluid may cause the contact layer 110 to float relative to the debris 130. As the contact layer 110 floats, it may change position relative to the position the contact layer 110 occupied during the negative-pressure therapy cycle. The position change may cause the contact layer 110 to engage a slightly different portion of the debris 130 during the next negative-pressure therapy cycle, aiding disruption of the debris 130.

In some embodiments, the contact layer 110 may be bonded to the retainer layer 108. In other embodiments, the retainer layer 108 may have a portion subjected to the compression or felting processes to form the contact layer 110. The plurality of through-holes 140 may then be formed or cut into the compressed foam portion of the retainer layer 108 to a depth for the desired height of the nodules 139. In other embodiments, the retainer layer 108 may be a compressed or felted foam having the through-holes 140 formed in a portion of the retainer layer 108. The portions of the retainer layer 108 having the through-holes 140 may comprise the contact layer 110.

In some embodiments, the contact layer 110 may be provided as a component of a dressing kit. The kit may include a punch, and the contact layer 110 may be provided without any through-holes 140. When using the contact layer 110, the user may use the punch to place the through-holes 140 through portions of the contact layer 110 that may be placed over the debris 130. The kit provides a user, such as a clinician, the ability to customize the contact layer 110 to the particular tissue site 103, so that the through-holes 140 are only disrupting the debris 130 and not healthy tissue that may be near or surround the debris 130.

The contact layer 110 can also be used with other foams without the through-holes 140. The contact layer 110 can be cut to fit the debris 130 at the tissue site 103, and dressing material without the through-holes 140 may be placed over remaining areas of the tissue site 103. Similarly, other dressing materials may be placed between the contact layer 110 and the tissue site 103 where no disruption is desired. In some embodiments, the kit may include a first retainer layer 108 having a thickness of between about 5 mm and about 15 mm and, more specifically, about 8 mm. The kit can also include a second retainer layer 108 having a thickness between about 10 mm and about 20 mm and, more specifically, about 16 mm. During application of the dressing 102, the user may select an appropriate one of the first retainer layer 108 and the second retainer layer 108 as needed to fill the tissue site 103.

In an experimental model, the contact layer 110 was evaluated on various matrices using a Dermosol wound model to simulate human tissue that allows contraction of the tissue during negative-pressure therapy. The matrices included a soluble Pectin matrix to simulate thick exudate or biofilm, a combination soluble and insoluble matrix to simulate slough and eschar, and an insoluble matrix, such as Prisma™, to simulate robust devitalized tissue. The experimental results indicated that the contact layer 110 provided granulation and particle loss comparable to negative-pressure therapy with a foam manifold, such as Granufoam®, with decrease in peel force and bleeding. In addition, the experimental results provided consistent visual evidence of surface changes related to the pattern of the through-holes 140 that results in loosening and detachment of exudate and infectious material.

Figure 10:
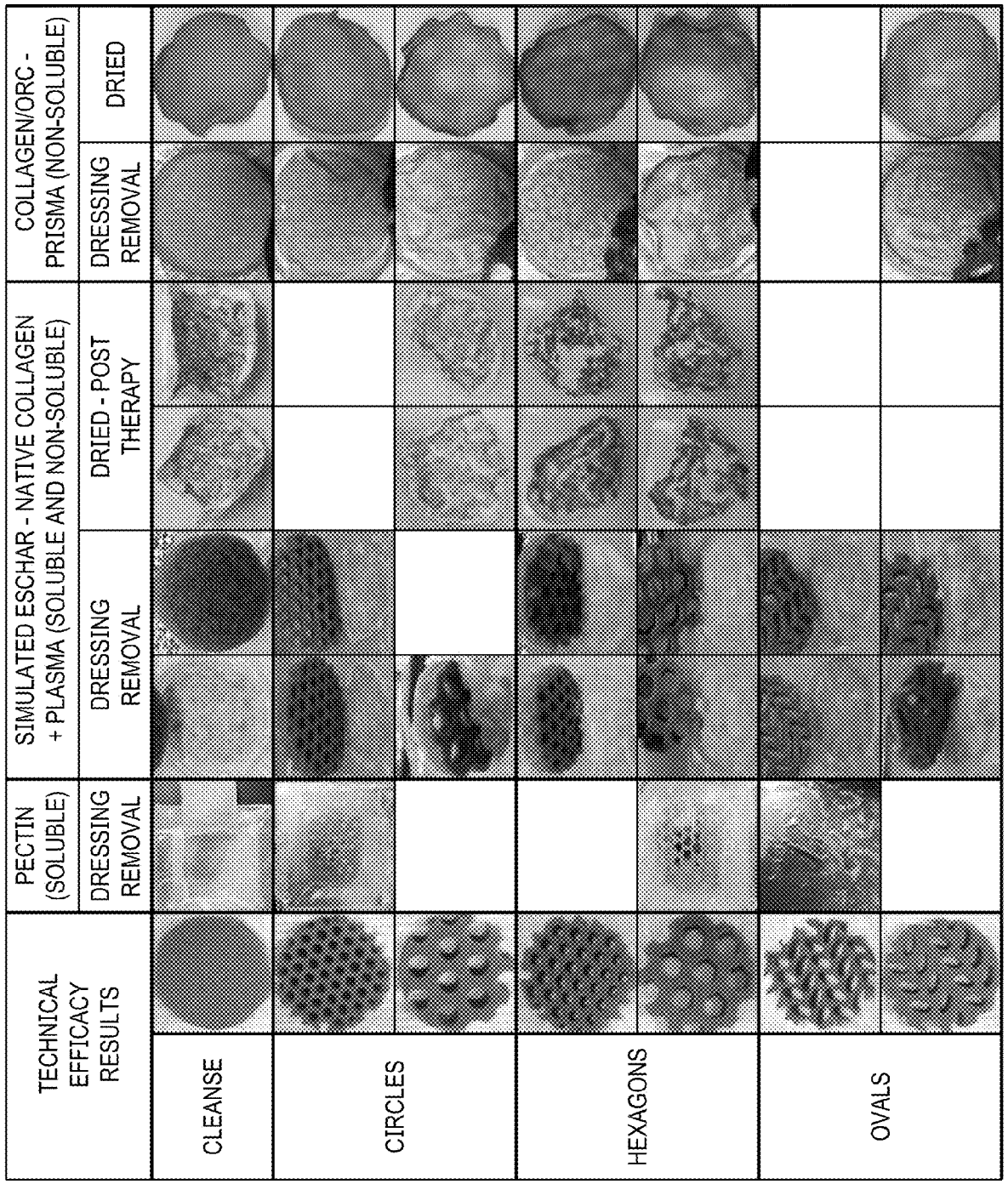
FIG. 10 is a color photograph, illustrating details that may be associated with an experimental embodiment of the contact layer.

In the experimental model, each matrix was 5 cm in diameter and had a 1 cm depth. Each matrix was maintained at a controlled temperature using heated circulated water. The Pectin matrices were subjected to a single cycle, each having a 10 minute instillation soak period and 30 minute negative pressure therapy period lasting for an experimental time period of about 1 hour. The simulated eschar matrices were subjected to 10 cycles, each having a 20 minute instillation soak period and 45 minute negative pressure therapy period for an experimental time period of about 10 hours. The collagen matrices were subjected to 48 cycles, each having a 20 minute instillation soak period and a 45 minute negative pressure therapy period for an experimental time period of about 48 hours. As illustrated in FIG. 10, in each experimental case, softening and other disruption of debris occurred.

In another experimental model, the effect on granulation tissue formation and tissue healing progression using negative-pressure therapy and instillation with the contact layer in a porcine model was studied. The model used full thickness dorsal excisional wounds having a rectangular shape. The wounds were 3 cm×7 cm in size on female domestic swine. The dressings used in the experimental model were changed every two to three days during a seven day study duration. Each animal included a control site dressed with a foam manifold, such as a Granufoam®, and saline instillation. Each animal had twelve tissue sites. 180 degree peel testing was conducted at each dressing change to determine the peel force required to remove the dressing and the amount of foam retention in the site. Histology was conducted at the termination of seven days to determine the granulation tissue thickness and to make a scored assessment of inflammation, abscess, and edema. The scored assessment used the following scale: 0 for the condition not being present, 1 for the condition being minimal, 2 for the condition being mild, 3 for the condition being moderate, 4 for the condition being marked, and 5 for the condition being severe. In addition, images were made of each tissue site at each dressing change to determine healing progression and the amount of retained foam. Treatment included a 10 minute instillation soak period, a 3.5 hour negative pressure therapy period at −125 mmHg, and 6.5 therapy cycles were conducted per day. Six experimental dressing types were tested. The through-holes in the contact layer in two dressings were circular. In the first, the through-holes had 4 mm diameters and 3 mm spacing between the perimeters of adjacent through-holes; in the second, the through-holes had 10 mm diameters and 5 mm spacing between the perimeters of adjacent through-holes. The through-holes in the contact layer in two dressings were hexagonal. In the first, the through-holes had 4 mm sides and 3 mm spacing between the perimeters of adjacent through-holes. In the second, the through-holes had 10 mm sides and 5 mm spacing between the perimeters of adjacent through-holes. The through-holes in the contact layer in two dressings were ellipsoid. In the first, the through-holes had a 10 mm×5 mm ellipse and small spacing, and in the second, the through-holes had a 5 mm×10 mm ellipse and large spacing.

The control group experienced an average of 5.1 Newtons (N) peel force on day 7 and maximum bleeding. Granulation tissue thickness was nominal, edema measured at 1.8, abscess at 0.5, and inflammation at 1.2. For the various contact layers described herein, the average peel force was less than 5.1 N at day 3, day 5, and day 7. In addition, the total amount of blood loss for the experimental dressings was 50% of the blood loss for the control dressings at day 7. The histological scores for the experimental contact layers were less than 3. In addition, granulation tissue thickness for the experimental dressings was measured at between 3 mm and 5 mm, where the granulation tissue thickness in the control dressings was about 4 mm.

Figure 11:
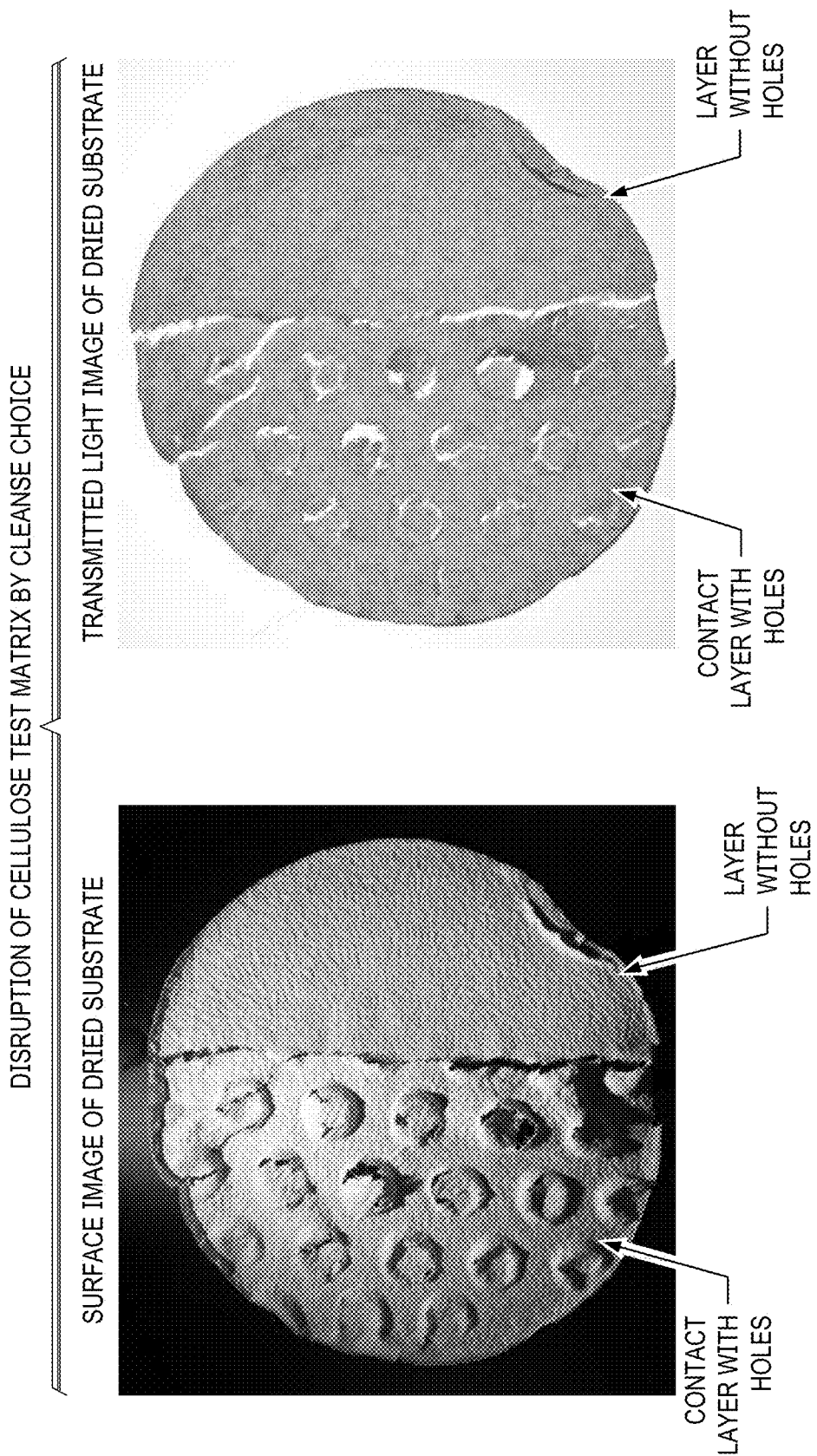
FIG. 11 is a color photograph, illustrating disruption of debris associated with use of the contact layer of FIG. 2.
Figure 12:
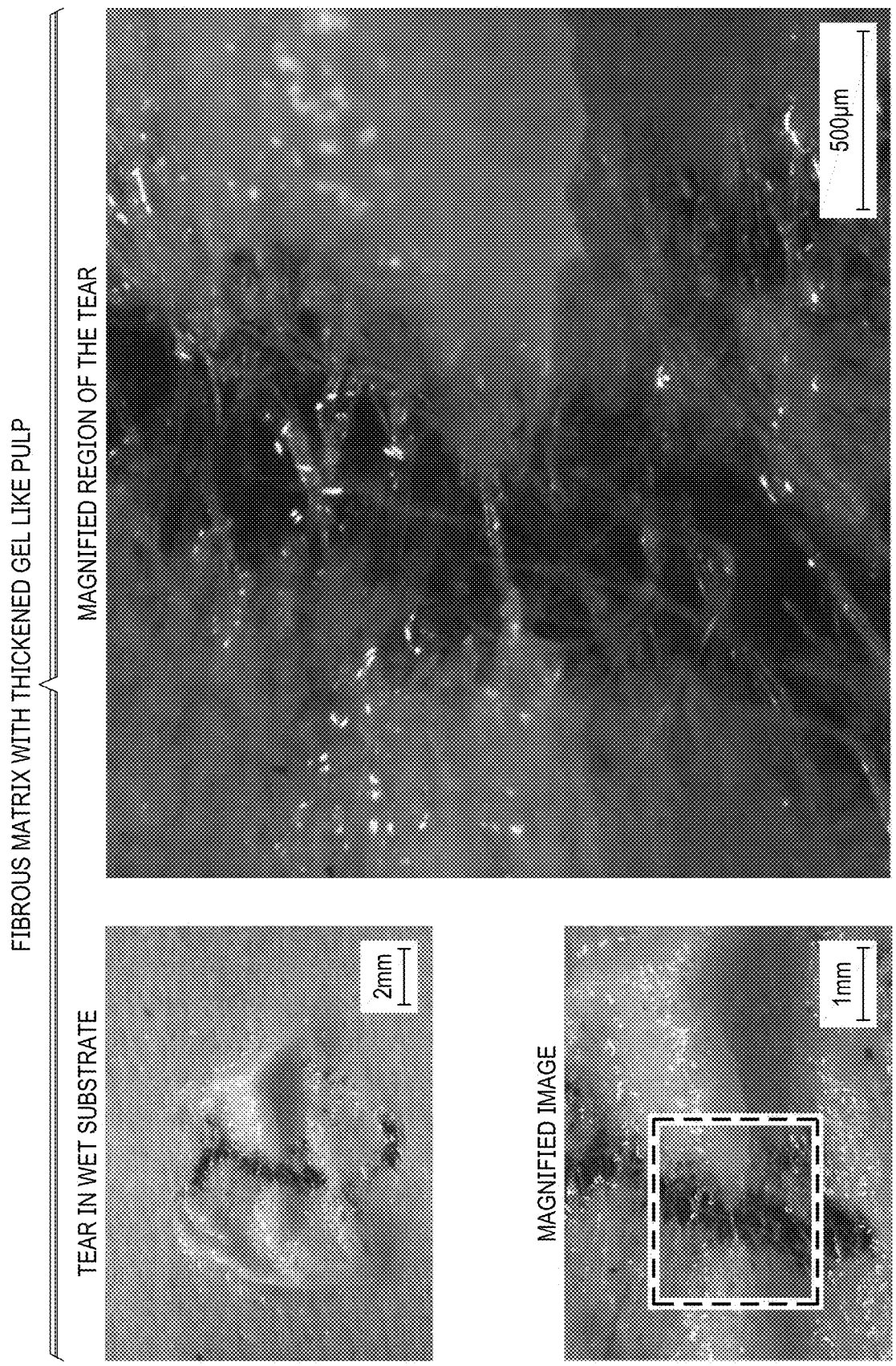
FIG. 12 is a color photograph, illustrating additional details associated with disruption of debris caused by use of the contact layer of FIG. 2.

Disruption of debris associated with other experimental results is illustrated in FIG. 11 and FIG. 12. As shown in FIG. 11, a cellulose test matrix was treated with a contact layer having circular holes and a foam material. The portion treated with the contact layer having circular holes demonstrated disruption of debris on the tissue following treatment. In contrast, the portion of the cellulose test matrix treated with a foam material experienced little to no disruption. FIG. 12 illustrates a magnified view of the cellulose test matrix of FIG. 11 showing the fibrous matrix having a thickened gel-like pulp. Following treatment with the contact layer, the fibrous matrix showed evidence of disruption including rupture of the matrix.

Figure 13:
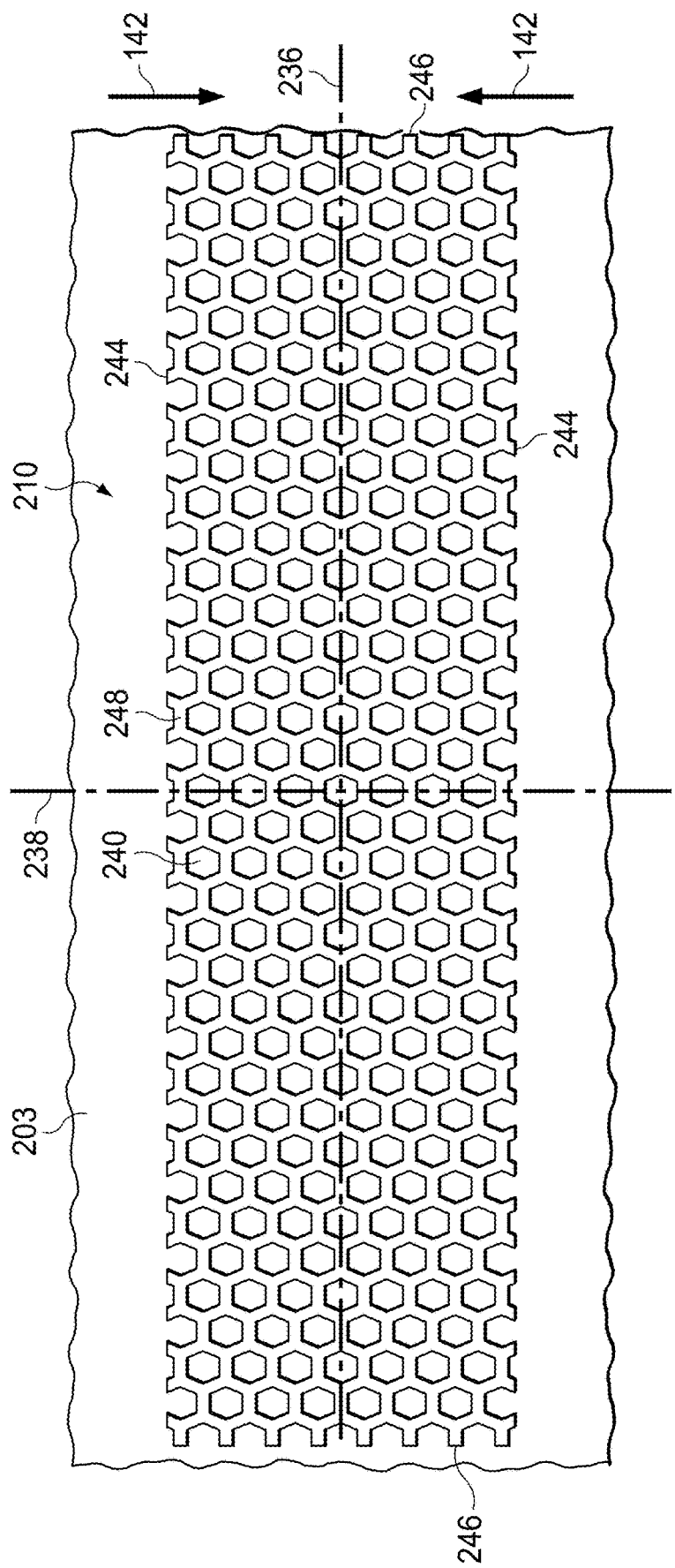
FIG. 13 is a plan view, illustrating details that may be associated with some embodiments of another contact layer of the therapy system of FIG. 1.

FIG. 13 is a plan view, illustrating additional details that may be associated with some embodiments of a contact layer 210. The contact layer 210 may be similar to the contact layer 110 and operate as described above with respect to FIGS. 1-9. Similar elements may have similar numbers indexed to 200. For example, the contact layer 210 is shown as having a generally rectangular shape including longitudinal edges 244 and latitudinal edges 246. The contact layer 210 may have a first orientation line 236 and a second orientation line 238 that is perpendicular to the first orientation line 236. The contact layer 210 may include a plurality of through-holes 240 or perforations extending through the contact layer 210 to from walls 248 that extend through the contact layer 210. The walls 248 may have interior or transverse surfaces that intersect with the tissue-facing surface 211 to form cutting edges. In some embodiments, the through-holes 240 may have a hexagonal shape as shown.

Figure 14:
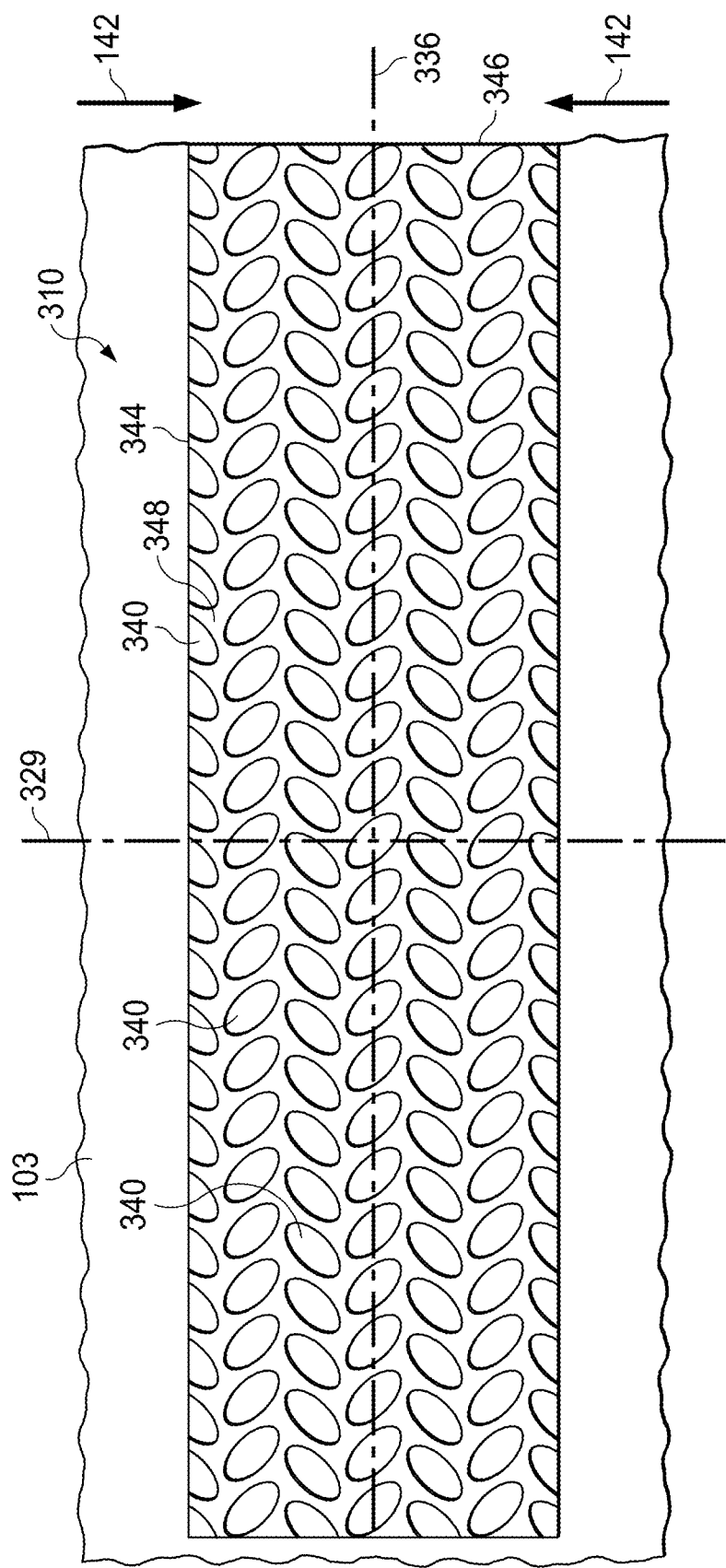
FIG. 14 is a plan view, illustrating details that may be associated with some embodiments of another contact layer of the therapy system of FIG. 1.

FIG. 14 is a plan view, illustrating additional details that may be associated with some embodiments of a contact layer 310. The contact layer 310 may be similar to the contact layer 110 and operate as described above with respect to FIGS. 1-9. Similar elements may have similar reference numbers indexed to 300. In some embodiments, the contact layer 310 may have a first orientation line 336 and a second orientation line 338 that is perpendicular to the first orientation line 336. The contact layer 310 may include a plurality of through-holes 340 or perforations extending through the contact layer 310 to form walls 348 that extend through the contact layer 310. The walls 348 may have interior surfaces or transverse surfaces that intersect with the tissue-facing surface 311 to form cutting edges. In some embodiments, the through-holes 340 may have an ovoid shape as shown.

Figure 15:
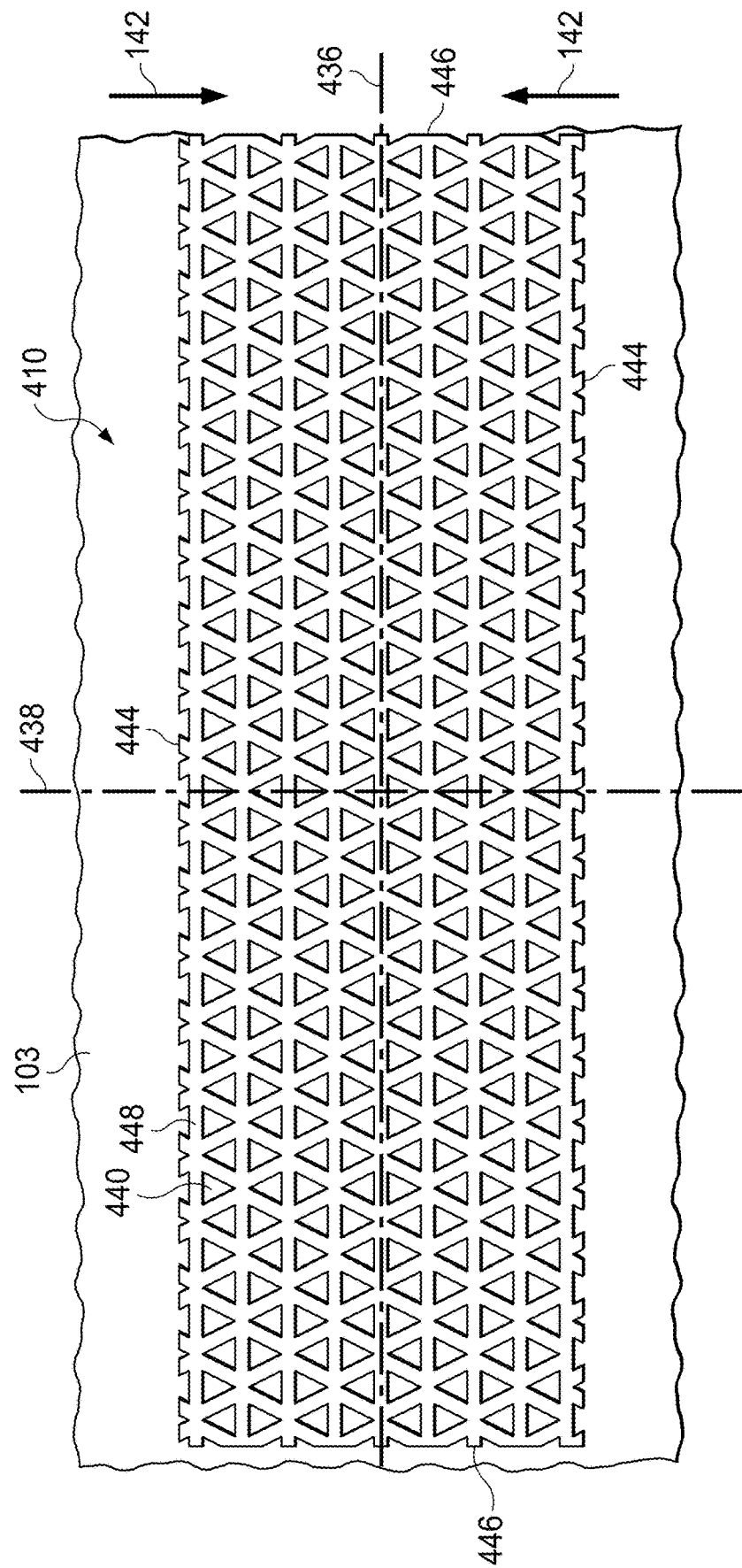
FIG. 15 is a plan view, illustrating details that may be associated with some embodiments of another contact layer of the therapy system of FIG. 1.

FIG. 15 is a plan view, illustrating additional details that may be associated with some embodiments of a contact layer 410. The contact layer 410 may be similar to the contact layer 110 and operate as described with respect to FIGS. 1-9. Similar elements may have similar reference numbers indexed to 400. For example, the contact layer 410 is shown as having a generally rectangular shape including longitudinal edges 444 and latitudinal edges 446. In some embodiments, the contact layer 410 may have a first orientation line 436 and a second orientation line 438 that is perpendicular to the first orientation line 436. The contact layer 410 may include a plurality of through-holes 440 or perforations extending through the contact layer 410 to form walls 448 that extend through the contact layer 410. The walls 448 may have interior surfaces or transverse surfaces that intersect with the tissue-facing surface 411 to form cutting edges. In some embodiments, the through-holes 440 may have a triangular shape as shown.

The through-holes 240, the through-holes 340, and the through-holes 440 of each of the contact layer 210, the contact layer 310, and the contact layer 410 may generate concentrated stresses that influence disruption of the debris 130 in different ways. For example, the triangular shaped through-holes 440 of the contact layer 410 may focus the stresses of the contact layer 410 at vertices of the through-holes 440 so that disruption of the debris 130 may be focused at the vertices of the through-holes 440. Similarly, the different shapes of the through-holes 240 and the through-holes 340 may also focus the stresses generated by the contact layer 210 and the contact layer 310 in other advantageous areas.

A lateral force, such as the lateral force 142, generated by a contact layer, such as the contact layer 110, may be related to a compressive force generated by applying negative pressure at a therapy pressure to a sealed therapeutic environment. For example, the lateral force 142 may be proportional to a product of a therapy pressure (TP) in the sealed therapeutic environment 128, the compressibility factor (CF) of the contact layer 110, and a surface area (A) the tissue-facing surface 111 of the contact layer 110. The relationship is expressed as follows:

$$\text{Lateral force } \alpha(TP*CF*A)$$

In some embodiments, the therapy pressure TP is measured in $N/m^2$, the compressibility factor (CF) is dimensionless, the area (A) is measured in $m^2$, and the lateral force is measured in Newtons (N). The compressibility factor (CF) resulting from the application of negative pressure to a contact layer may be, for example, a dimensionless number that is proportional to the product of the void space percentage (VS) of a contact layer, the firmness factor (FF) of the contact layer, the strut angle (SA) of the through-holes in the contact layer, and the perforation shape factor (PSF) of the through-holes in the contact layer. The relationship is expressed as follows:

$$\text{Compressibility Factor (CF)}\alpha(VS*FF*\sin(SA)*PSF)$$

Based on the above formulas, contact layers formed from different materials with through-holes of different shapes were manufactured and tested to determine the lateral force of the contact layers. For each contact layer, the therapy pressure TP was about −125 mmHg and the dimensions of the contact layer were about 200 mm by about 53 mm so that the surface area (A) of the tissue-facing surface of the contact layer was about 106 $cm^2$ or 0.0106 $m^2$. Based on the two equations described above, the lateral force for a Supracor® contact layer 210 having a firmness factor (FF) of 3 was about 13.3 where the Supracor® contact layer 210 had hexagonal through-holes 240 with a distance between opposite vertices of 5 mm, a perforation shape factor (PSF) of 1.07, a strut angle (SA) of approximately 66°, and a void space percentage (VS) of about 55%. A similarly dimensioned GranuFoam® contact layer 110 generated the lateral force 142 of about 9.1 Newtons (N).

TABLE 1

| Material | VS | FF | SA | Hole Shape | PSF | Major diam. (mm) | Lateral force |
|---|---|---|---|---|---|---|---|
| GranuFoam ® | 56 | 5 | 47 | Ovular | 1 | 10 | 13.5 |
| Supracor ® | 55 | 3 | 66 | Hexagon | 1.1 | 5 | 13.3 |
| GranuFoam ® | 40 | 5 | 63 | Triangle | 1.1 | 10 | 12.2 |
| GranuFoam ® | 54 | 5 | 37 | Circular | 1 | 5 | 11.9 |
| GranuFoam ® | 52 | 5 | 37 | Circular | 1 | 20 | 10.3 |
| Grey Foam | N/A | 5 | N/A | Horizontal stripes | N/A | N/A | 9.2 |
| GranuFoam ® | 55 | 5 | 66 | Hexagon | 1.1 | 5 | 9.1 |
| GranuFoam ® | N/A | 5 | N/A | Horizontal stripes | N/A | N/A | 8.8 |
| Zotefoam | 52 | 3 | 37 | Circular | 1 | 10 | 8.4 |
| GranuFoam ® | 52 | 5 | 37 | Circular | 1 | 10 | 8.0 |
| GranuFoam ® | 52 | 5 | 64 | Circular | 1 | 10 | 7.7 |
| GranuFoam ® | 56 | 5 | 66 | Hexagon | 1.1 | 10 | 7.5 |
| Grey Foam | N/A | 3 | N/A | Horizontal stripes | N/A | N/A | 7.2 |
| Zotefoam | 52 | 3 | 52 | Circular | 1 | 20 | 6.8 |
| GranuFoam ® | N/A | 3 | N/A | Horizontal Striping | N/A | N/A | 6.6 |
| GranuFoam ® | 52 | 5 | 52 | Circular | 1 | 20 | 6.5 |
| GranuFoam ® | N/A | 5 | N/A | Vertical Stripes | N/A | N/A | 6.1 |
| GranuFoam ® | N/A | 1 | N/A | None | N/A | N/A | 5.9 |
| GranuFoam ® | N/A | 3 | N/A | Vertical stripes | N/A | N/A | 5.6 |
| GranuFoam ® | 52 | 1 | 37 | None | 1 | 10 | 5.5 |

In some embodiments, the formulas described above may not precisely describe the lateral forces due to losses in force due to the transfer of the force from the contact layer to the wound. For example, the modulus and stretching of the drape 106, the modulus of the tissue site 103, slippage of the drape 106 over the tissue site 103, and friction between the contact layer 110 and the tissue site 103 may cause the actual value of the lateral force 142 to be less than the calculated value of the lateral force 142.

FIG. 16 is a flow chart 1600 illustrating exemplary operations that can be associated with some embodiments of the therapy system 100 of FIG. 1. At block 1601, the contact layer 110 may be selected for use on the tissue site 103.

At block 1603, the selected contact layer can be positioned at a tissue site. For example, the contact layer 110 can be positioned over the debris 130 of the tissue site 103. At block 1605, a retainer layer may be selected for use on the tissue site. For example, the retainer layer 108 can be selected for use on the tissue site 103. At block 1607, the selected retainer layer can be positioned over the contact layer. For example, the retainer layer 108 can be positioned over the contact layer 110. At block 1609, a sealing member may be positioned over the retainer layer, the contact layer, and the tissue site, and at block 1611, the sealing member can be sealed to tissue surrounding the tissue site. For example, the drape 106 can be positioned over the tissue site 103 and sealed to tissue surrounding the tissue site 103.

At block 1613, a negative pressure source can be fluidly coupled to a sealed space formed by the sealing member. For example, the negative-pressure source 104 can be fluidly coupled to the sealed therapeutic environment 128 formed by the drape 106. At block 1615, the negative-pressure source can supply negative pressure to the sealed space. For example, a controller of the negative-pressure source 104 can actuate the negative-pressure source 104 to draw fluid from the sealed therapeutic environment 128, thereby supplying negative-pressure to the sealed therapeutic environment 128 for a negative-pressure therapy period.

At block 1617, the controller can determine if the negative-pressure therapy period has concluded. For example, a controller of the negative-pressure source 104 can determine if a timer, started when the negative-pressure source was actuated to supply negative pressure, has reached a predetermined time. The predetermined time may be based on an expected timer interval for negative-pressure therapy of the predetermined time may be a time period selected by a user. At block 1617, if the timer has not expired, the method can continue on the NO path to block 1615, where the controller of the negative-pressure source can continue supplying negative pressure to the sealed space.

At block 1617, if the timer has expired, the method can continue on the YES path to block 1619, where the controller of the negative-pressure source can vent the negative pressure in the sealed space to the ambient environment. For example, the controller of the negative-pressure source 104 can vent the sealed therapeutic environment 128 to the ambient environment.

At block 1621, the method determines if therapy has concluded. For example, the controller of the negative-pressure source 104 can determine if a predetermined number of supply and vent cycles has been completed. The predetermined number of supply and vent cycles can be a standard number of cycles for therapy or can be a number of cycles entered in by a user. If therapy has not concluded, the method can continue on the NO path to block 1615, where the negative-pressure source can be operated to supply negative pressure to the sealed space. If therapy has concluded, the method can continue on the YES path, where the method ends.

FIG. 17 is a flow chart 1700 illustrating exemplary operations that can be associated with some embodiments of the therapy system 100 of FIG. 1. For example, operations may be implemented by a controller in a negative-pressure source, such as the negative-pressure source 104, configured to execute the operations. Operations may also be performed by a user, such as a clinician. At block 1701, a user may examine a tissue site. For example, a clinician may examine the tissue site 103.

At block 1703, the user may determine, based on the user's examination, a status of the debris of the tissue site. For example, a clinician may determine that the debris 130 covers the tissue site 103. The status determination can also include: a thickness of the debris 130, a consistency of the debris 130, a color of the debris 130, and a moisture level of the debris 130. For example, the clinician may determine that the debris 130 at the tissue site 103 may have a thin, thick, runny, solid, rough, firm, smooth, heavy, or light consistency. The clinician may determine that the debris 130 at the tissue site 103 has a black, red, brown, green, yellow, gray, or other color that is indicative of a state of infection of the debris 130. The clinician can also determine how moist the debris 130 at the tissue site 103 is on a scale ranging from no presence of liquid to saturated. In some embodiments, the determination of a moisture level aids a clinician in understanding how much exudate is present in the tissue site 103.

At block 1705, the user may determine other parameters influencing treatment. For example, the clinician can determine a patient's pain tolerance, environment, preference, age, co-morbidities, quality of life, caregiver resources, and caregiver skills.

At block 1707, based on the information determined at block 1703 and block 1705, the user can determine the desired targets for treatment of the debris at the tissue site. For example, the clinician can determine if the debris 130 comprises necrotic tissue, eschar, impaired tissue, other sources of infection, exudate, slough including hyperkeratosis, pus, foreign bodies, biofilm, or other types of bioburden. The clinician can also determine if treatment will reduce unpleasant odors, excess moisture, and the risk of infection of the debris 130 and the tissue site 103.

At block 1709, in response to the determination of the desired targets for treatment of the debris at the tissue site, the user can select a contact layer having a firmness factor, a thickness, a through-hole shape, a through-hole size, and an array pattern to achieve the desired targets for treatment. For example, the clinician may select the contact layer 110 to have the thickness 134 greater than the thickness determine at block 1703. The clinician can also select the contact layer 110 having circular through-holes 140 to permit the flow of the debris 130 having a yellowish color, a thick consistency, and a high moisture level. The clinician can further select a contact layer 110 having the through-holes 140 having a diameter greater than a size of the largest solubilized debris 130 in the tissue site 103. In other embodiments, the clinician may select a contact layer 110 having triangular through-holes 140, for example, if the debris 130 is rough, black, and has a low moisture content.

At block 1711, in response to the determination of the desired targets for treatment of the debris at the tissue site, the user can select a retainer layer. For example, the clinician can select the retainer layer 108 having a firmness factor and a thickness. Generally, the thickness of the retainer layer 108 may be selected to fill the tissue site 103. The clinician may select the firmness factor of the retainer layer 108 to limit the height of the nodules 139. For example, if the debris 130 is thinner than the contact layer 110, has a runny consistency, and has a smooth surface, the clinician may select a retainer layer 108 having a low firmness factor. A lower firmness factor of the retainer layer 108 may permit the bosses 137 to have a larger height than a retainer layer 108 having a high firmness factor, thereby decreasing the height of the nodules 139. At block 1713, the user may conduct treatment with contact layer. For example, the clinician may conduct treatment with the contact layer 110 and the therapy system 100, after which the method concludes.

The systems, apparatuses, and methods described herein may provide significant advantages. For example, combining the mechanical rubbing action of a contact layer with the hydrating and flushing action of instillation and negative-pressure therapy may enable low or no pain debridement of a tissue site. A contact layer as described herein may also require less monitoring from a clinician or other attendant as compared to other mechanical debridement processes and enzymatic debridement processes. In addition, contact layers as described herein may not become blocked by removed necrotic tissue as may occur during autolytic debridement of a tissue site. Furthermore, the contact layers described herein can aid in removal of necrosis, eschar, impaired tissue, sources of infection, exudate, slough including hyperkeratosis, pus, foreign bodies, debris, and other types of bioburden or barriers to healing. The contact layers can also decrease odor, excess wound moisture, and the risk of infection while stimulating edges of a tissue site and epithelialization. The contact layers described herein can also provide improved removal of thick exudate, allow for earlier placement of instillation and negative-pressure therapy devices, may limit or prevent the use of other debridement processes, and can be used on tissue sites that are difficult to debride.

In some embodiments, the therapy system may be used in conjunction with other tissue removal and debridement techniques. For example, the therapy system may be used prior to enzymatic debridement to soften the debris. In another example, mechanical debridement may be used to remove a portion of the debris at the tissue site, and the therapy system may then be used to remove the remaining debris while reducing the risk of trauma to the tissue site.

While shown in a few illustrative embodiments, a person having ordinary skill in the art will recognized that the systems, apparatuses, and methods described herein are susceptible to various changes and modifications. Moreover, descriptions of various alternatives using terms such as "or" do not require mutual exclusivity unless clearly required by the context, and the indefinite articles "a" or "an" do not limit the subject to a single instance unless clearly required by the context.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. A system for debriding a tissue site, comprising:
   a cover adapted to form a sealed space over the tissue site for receiving a negative pressure from a negative-pressure source; and
   a tissue interface having a manifold and a debridement tool, the manifold and the debridement tool being integral components of the tissue interface;
   the manifold adapted to deliver negative pressure to the tissue site;
   the debridement tool adapted to be positioned between the manifold and the tissue site, the debridement tool comprising a felted foam;

a plurality of holes extending through the debridement tool, the plurality of holes being separated from each other by walls, the walls having transverse surfaces extending perpendicular to a surface of the debridement tool that form cutting edges with the surface of the debridement tool, and wherein the plurality of holes have a perforation shape factor that allows the plurality of holes to collapse from a relaxed position to a contracted position in response to an application of negative pressure to the sealed space and to return from the contracted position to the relaxed position in response to a removal of negative pressure from the sealed space; and the plurality of holes being adapted to generate macro-pressure points in the tissue site in the contracted position and the cutting edges being adapted to disrupt the macro-pressure points in the tissue site in response to movement of the debridement tool between the relaxed position and the contracted position.

2. The system of claim 1, wherein the plurality of holes are adapted to collapse from the relaxed position to the contracted position generally perpendicular to a line of symmetry of the debridement tool.

3. The system of claim 1, wherein the plurality of holes have the perforation shape factor and a strut angle adapted to collapse the plurality of holes from the relaxed position to the contracted position.

4. The system of claim 3, wherein the strut angle is about 90 degrees.

5. The system of claim 3, wherein the strut angle is less than about 90 degrees.

6. The system of claim 1, wherein:
the plurality of holes are adapted to have the perforation shape factor and a strut angle that allows the plurality of holes to collapse from the relaxed position to the contracted position; and
the plurality of holes are adapted to collapse from the relaxed position to the contracted position generally perpendicular to a line of symmetry of the debridement tool.

7. The system of claim 1, further comprising a fluid source adapted to be fluidly coupled to the sealed space to provide fluid to the sealed space.

8. The system of claim 1, wherein the plurality of holes have an average effective diameter of about 5 mm.

9. The system of claim 1, wherein the plurality of holes are formed in two or more parallel rows.

10. The system of claim 1, wherein the perforation shape factor of each hole of the plurality of holes is less than about 1.

11. The system of claim 1, wherein a thickness of the debridement tool is about 15 mm.

12. The system of claim 1, wherein a firmness factor of the debridement tool is about 5.

13. The system of claim 1, wherein a firmness factor of the debridement tool is about 3.

14. The system of claim 1, wherein a shape of each hole of the plurality of holes is hexagonal.

15. The system of claim 1, wherein a shape of each hole of the plurality of holes is elliptical.

16. The system of claim 1, wherein a shape of each hole of the plurality of holes is circular.

17. The system of claim 1, wherein a shape of each hole of the plurality of holes is triangular.

* * * * *